United States Patent [19]
Kim

[11] Patent Number: 5,676,670
[45] Date of Patent: Oct. 14, 1997

[54] CATHETER APPARATUS AND METHOD FOR CREATING A VASCULAR BYPASS IN-VIVO

[75] Inventor: Ducksoo Kim, Dover, Mass.

[73] Assignee: Beth Israel Deaconess Medical Center, Boston, Mass.

[21] Appl. No.: 664,165

[22] Filed: Jun. 14, 1996

[51] Int. Cl.⁶ .................................................. A61F 11/00
[52] U.S. Cl. ......................... 606/108; 606/198; 606/186; 606/185; 606/194
[58] Field of Search .................................. 606/108, 191, 606/192, 194, 195, 198, 159, 170, 167, 185, 184

[56] References Cited

U.S. PATENT DOCUMENTS

| | | | |
|---|---|---|---|
| 4,577,631 | 3/1986 | Kreamer | 606/108 |
| 4,861,330 | 8/1989 | Voss | 606/194 |
| 5,015,238 | 5/1991 | Solomon et al. | 604/164 |
| 5,089,006 | 2/1992 | Stiles | 606/198 |
| 5,217,474 | 6/1993 | Zacca et al. | 606/170 |
| 5,250,060 | 10/1993 | Carbo et al. | 606/170 |
| 5,395,311 | 3/1995 | Andrews | 606/159 |
| 5,556,405 | 9/1996 | Lary | 606/159 |

Primary Examiner—Robert A. Hafer
Assistant Examiner—Justine R. Yu
Attorney, Agent, or Firm—Davd Prashker

[57] ABSTRACT

The present invention provides a catheter apparatus, an introducer system, and a methodology for creating a vascular bypass on-demand between an unobstructed blood vessel such as the aorta and an obstructed blood vessel such as an obstructed coronary artery in-vivo using a previously excised vascular segment as a shunt. The invention allows the placement and creation of single or multiple vascular grafts without use of a heart-lung machine and without need for stopping the heart of the patient during the coronary artery bypass surgery.

12 Claims, 25 Drawing Sheets

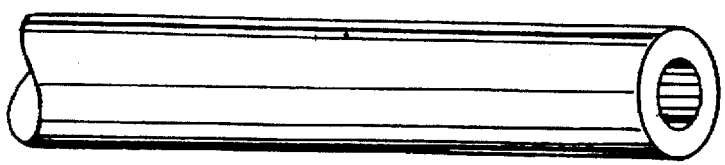 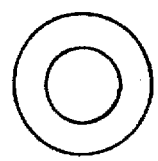
FIG. 3A  FIG. 3B
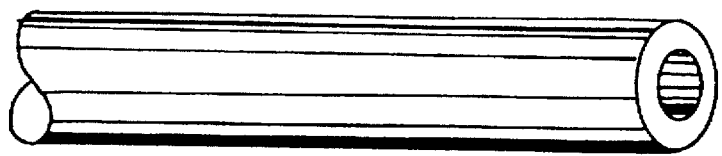 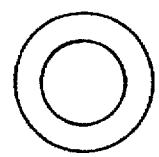
FIG. 4A  FIG. 4B
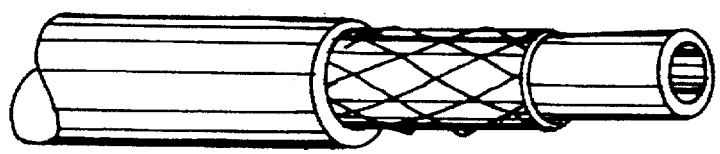 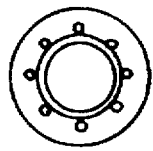
FIG. 5A  FIG. 5B
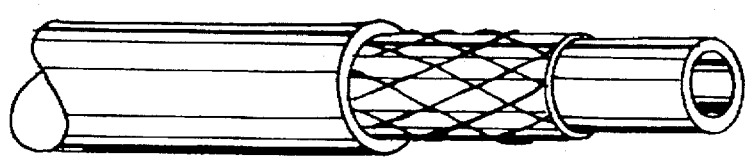 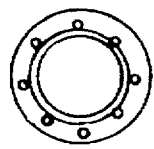
FIG. 6A  FIG. 6B

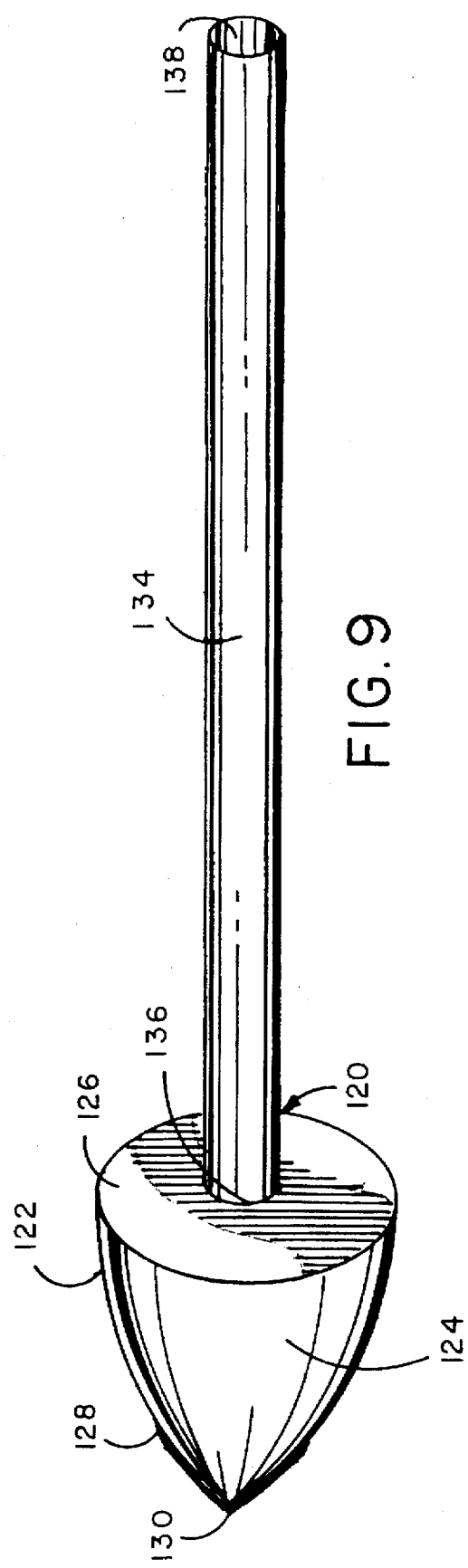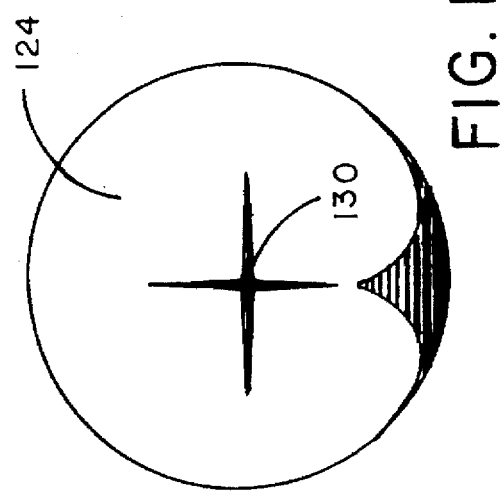

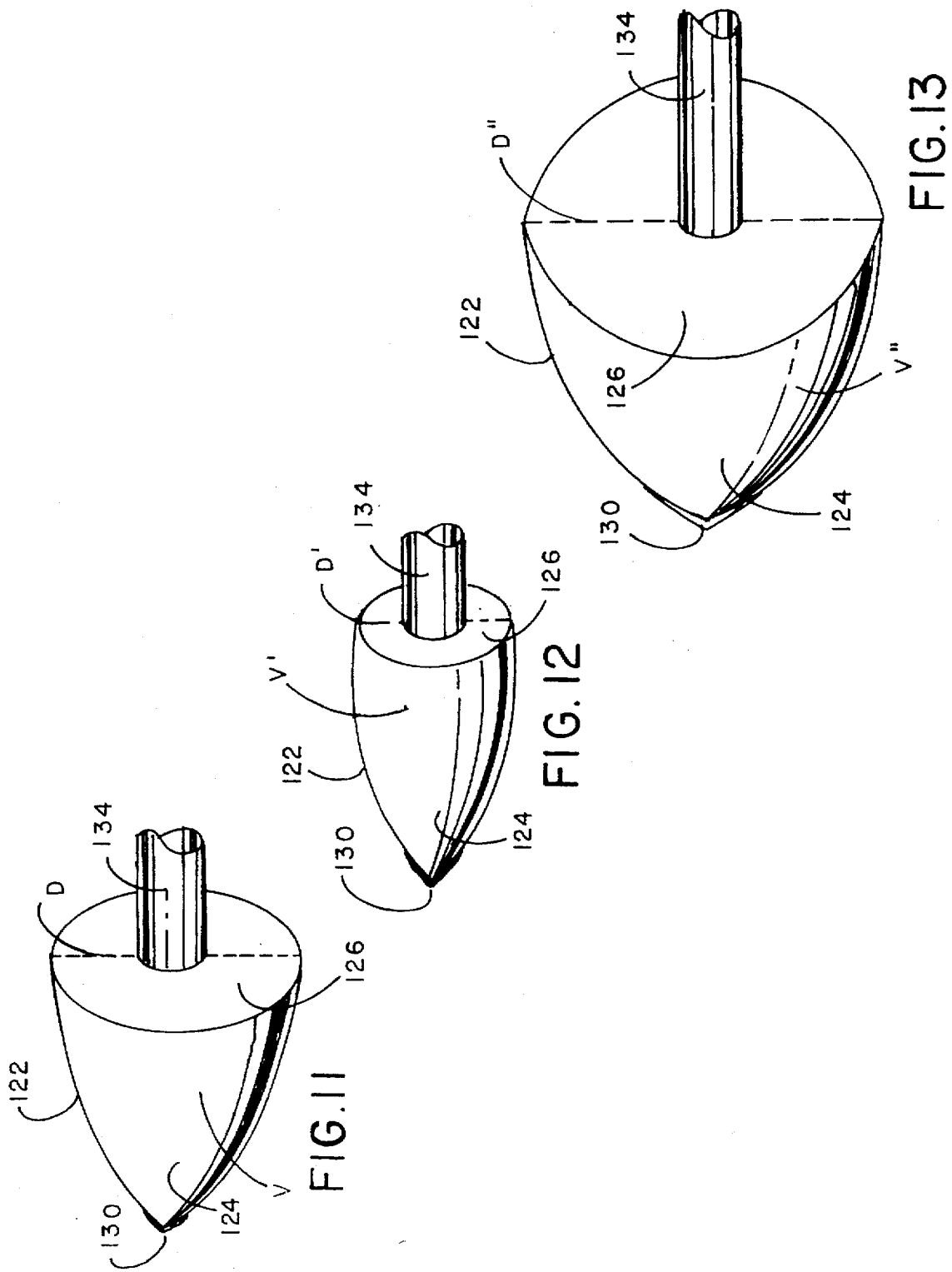

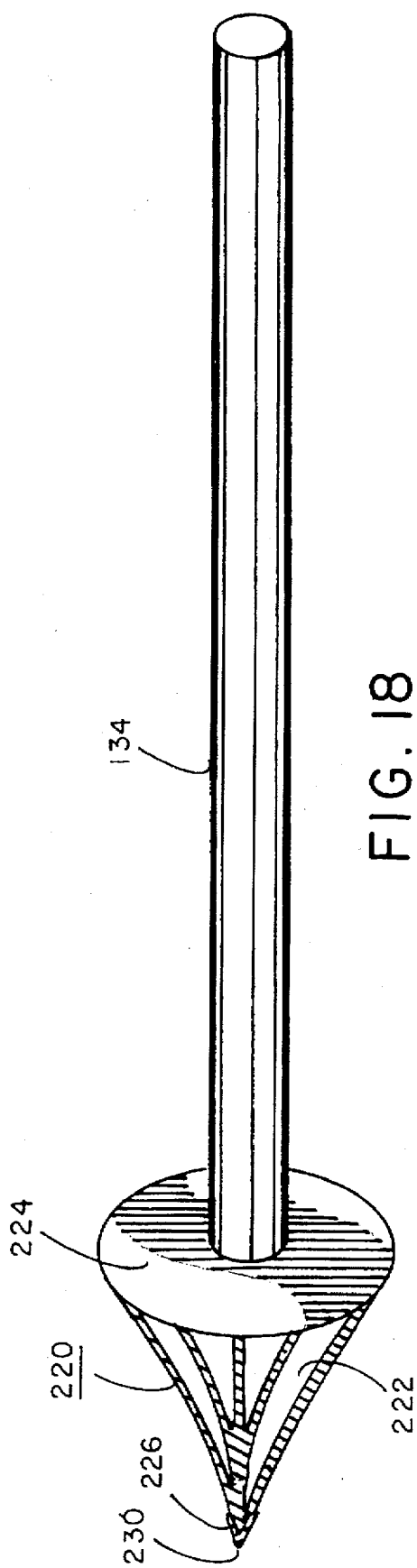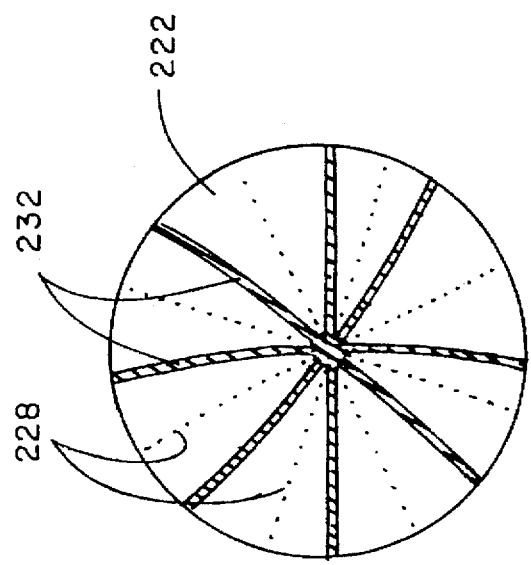
FIG. 18
FIG. 19

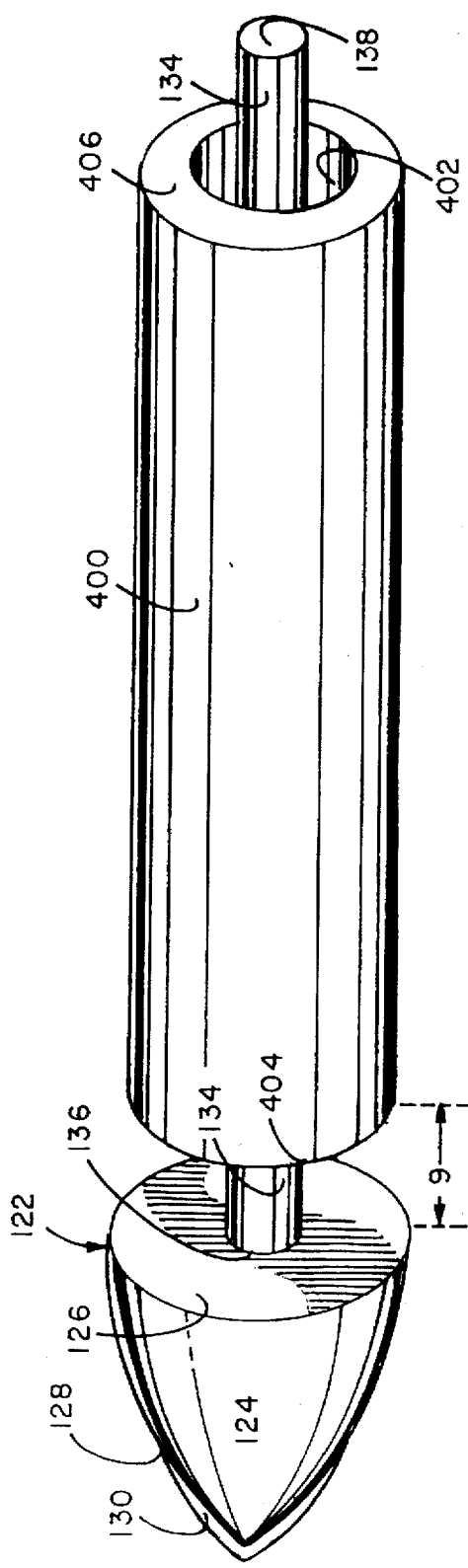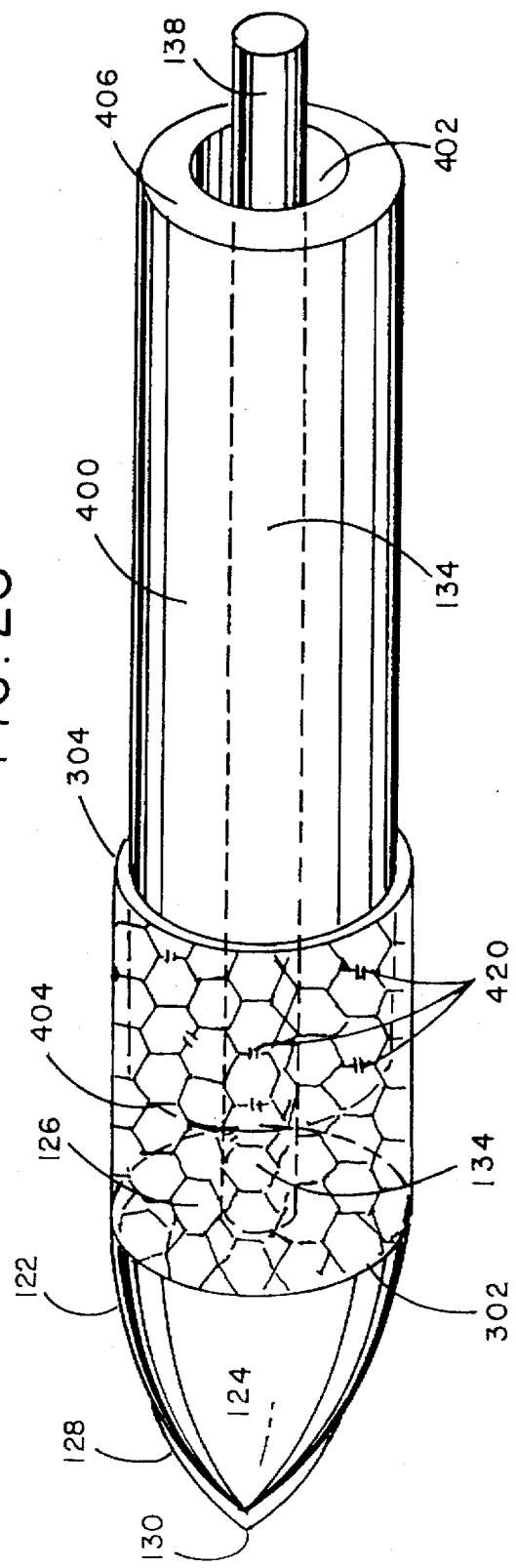

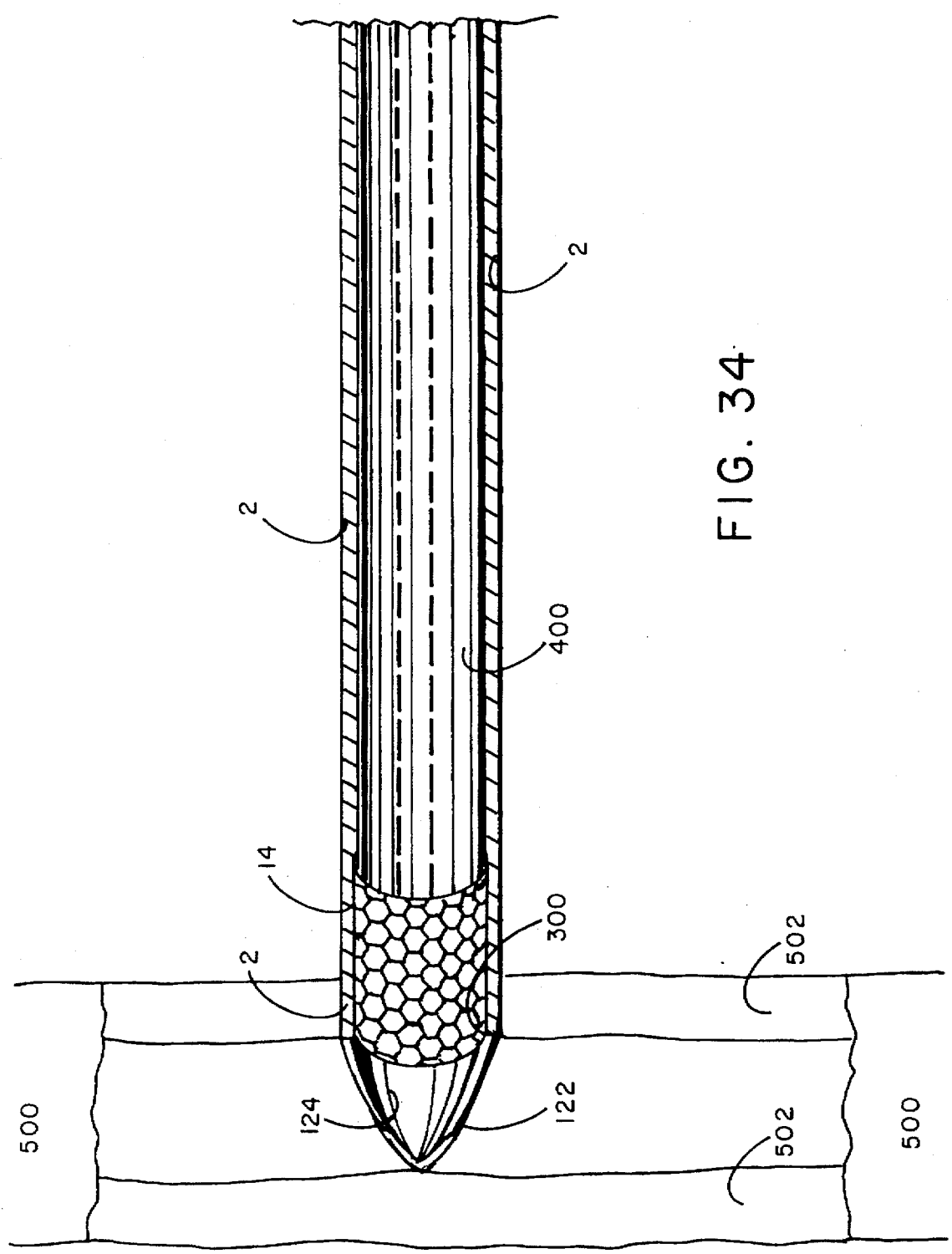

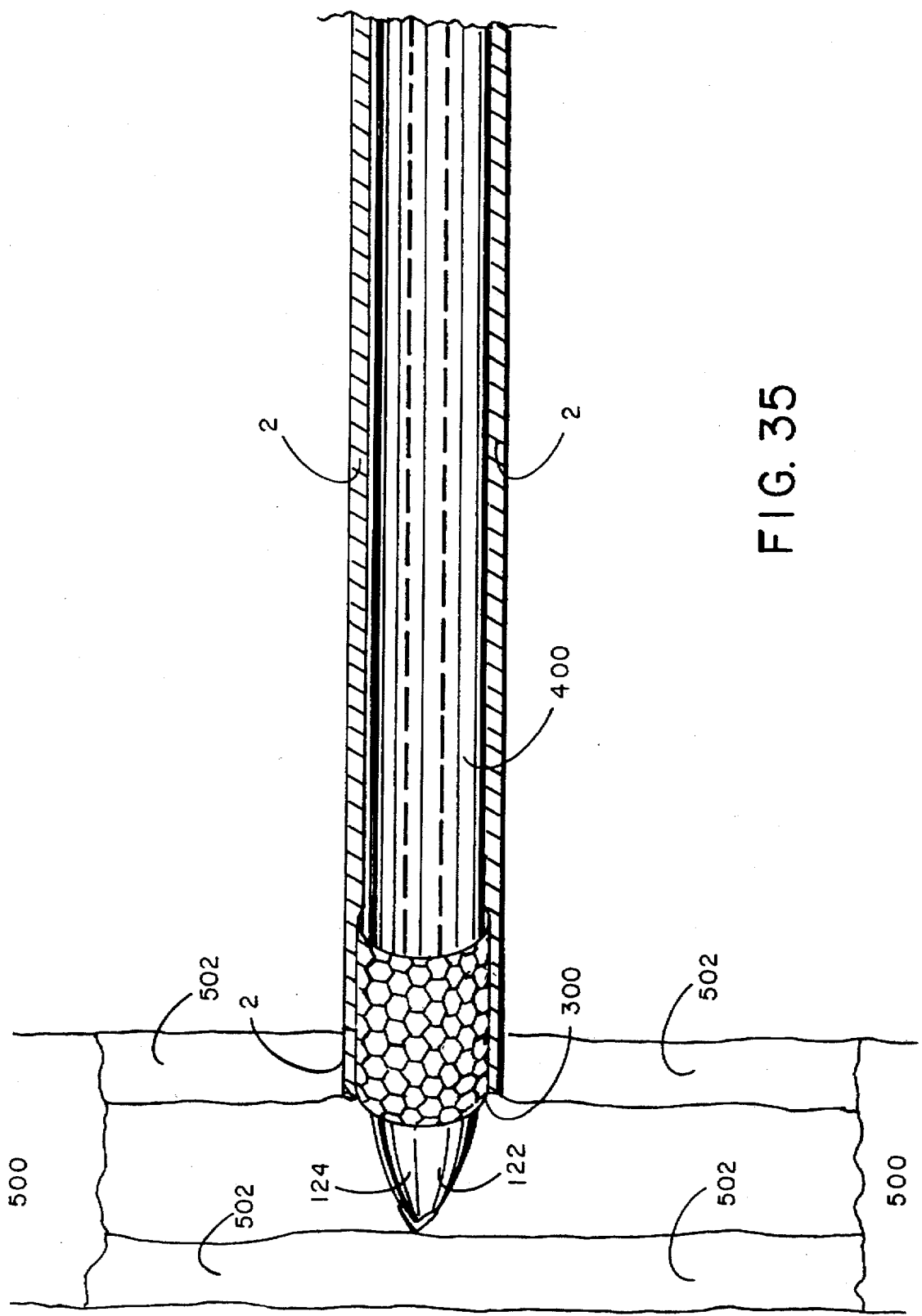

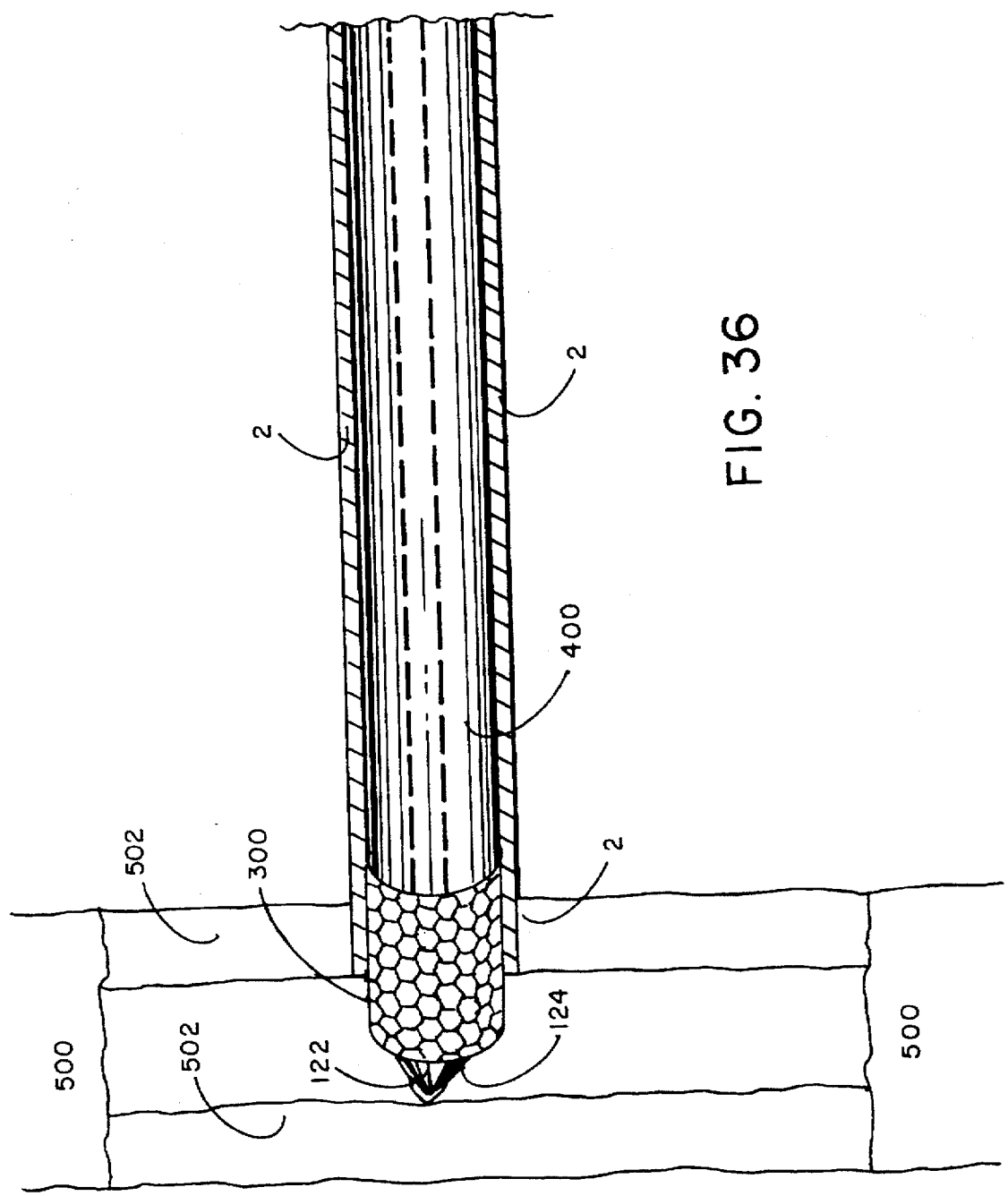

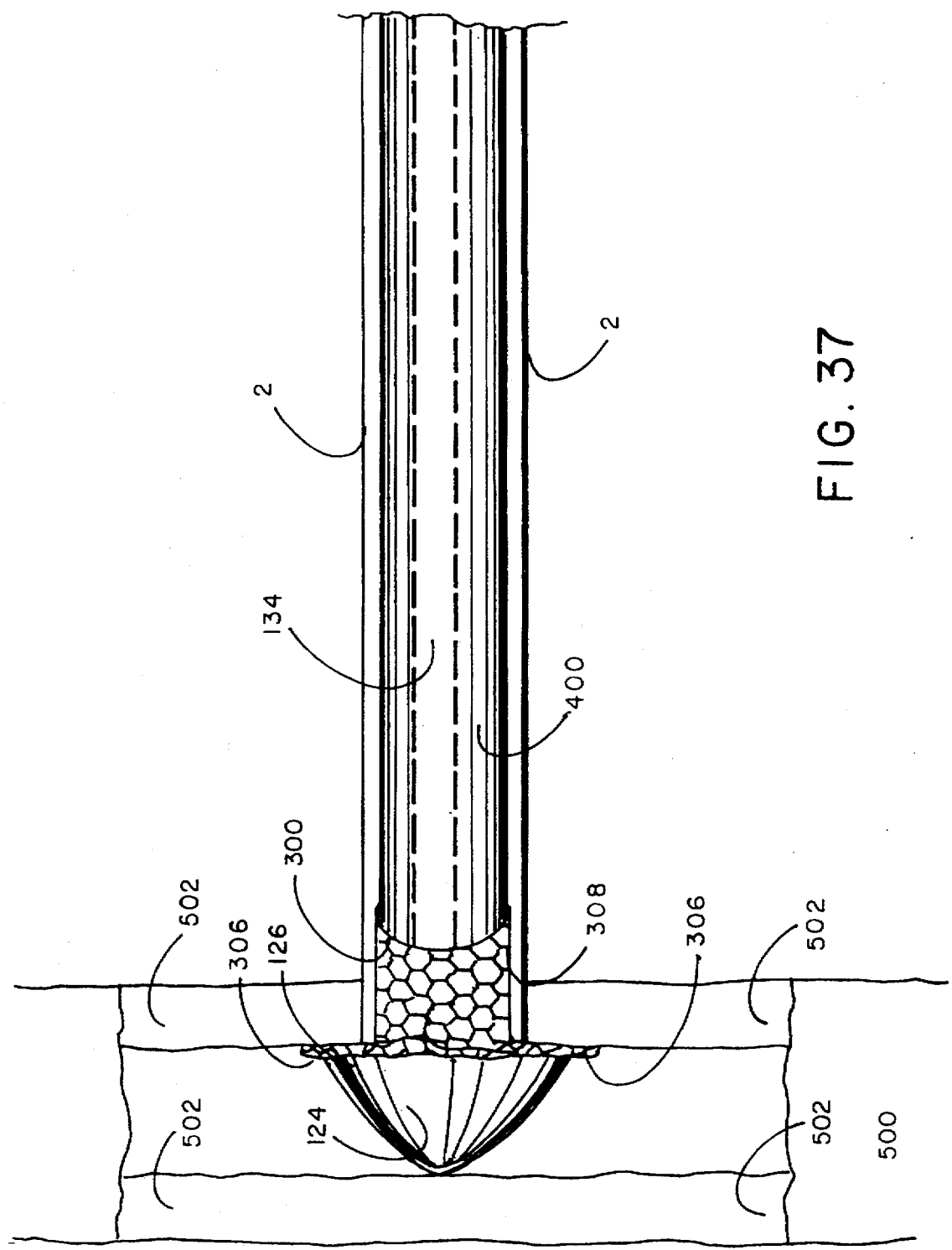

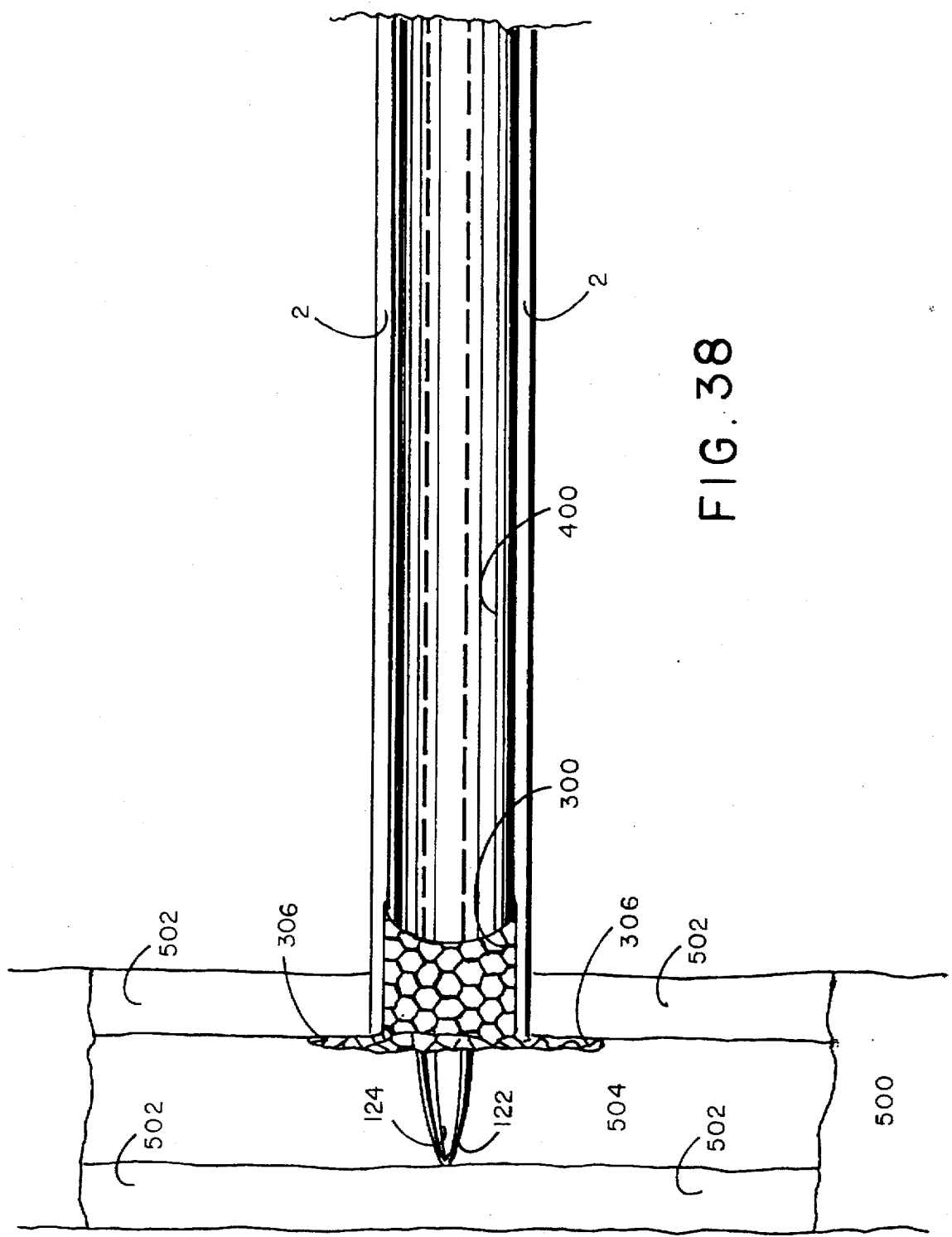

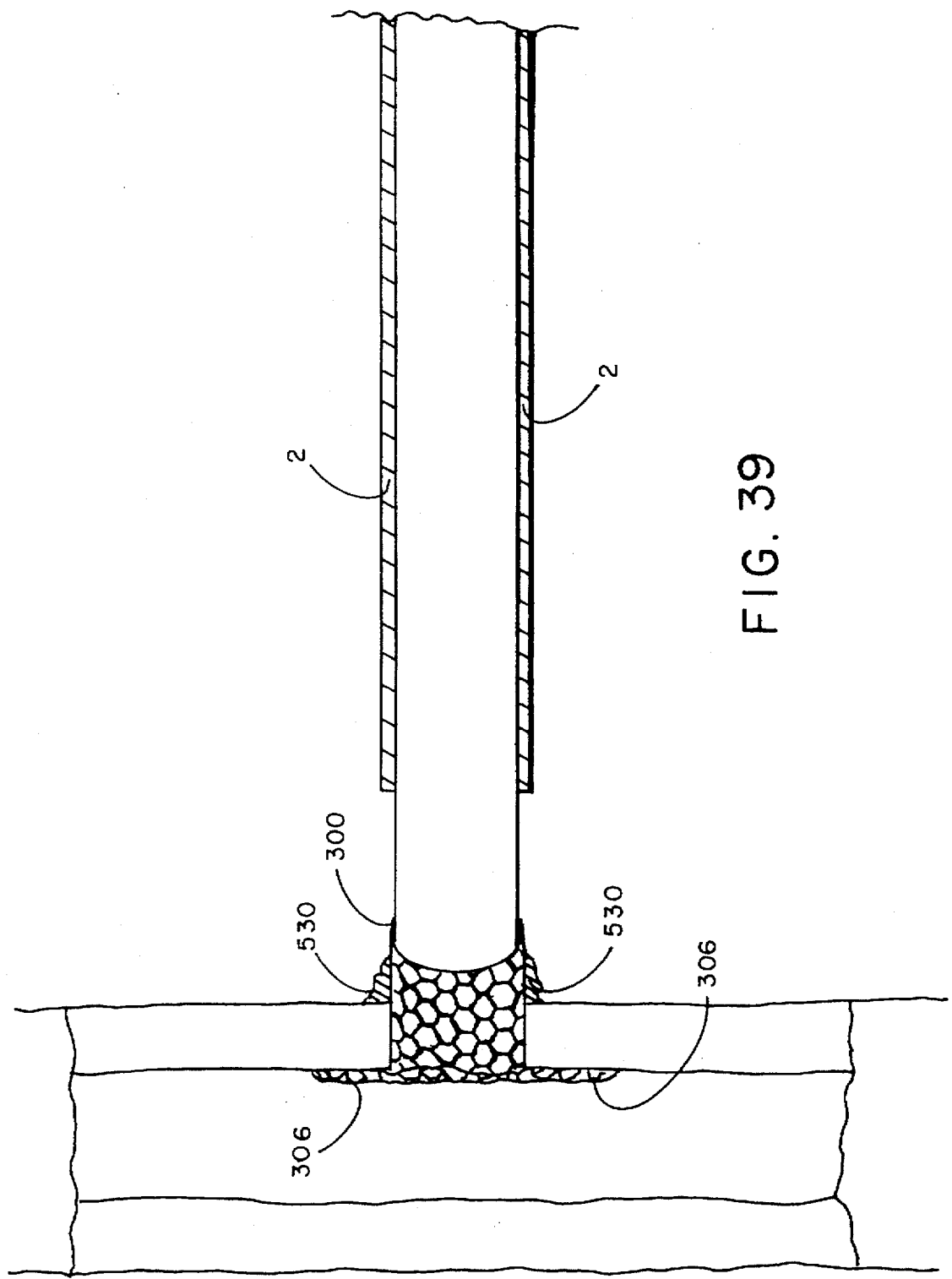

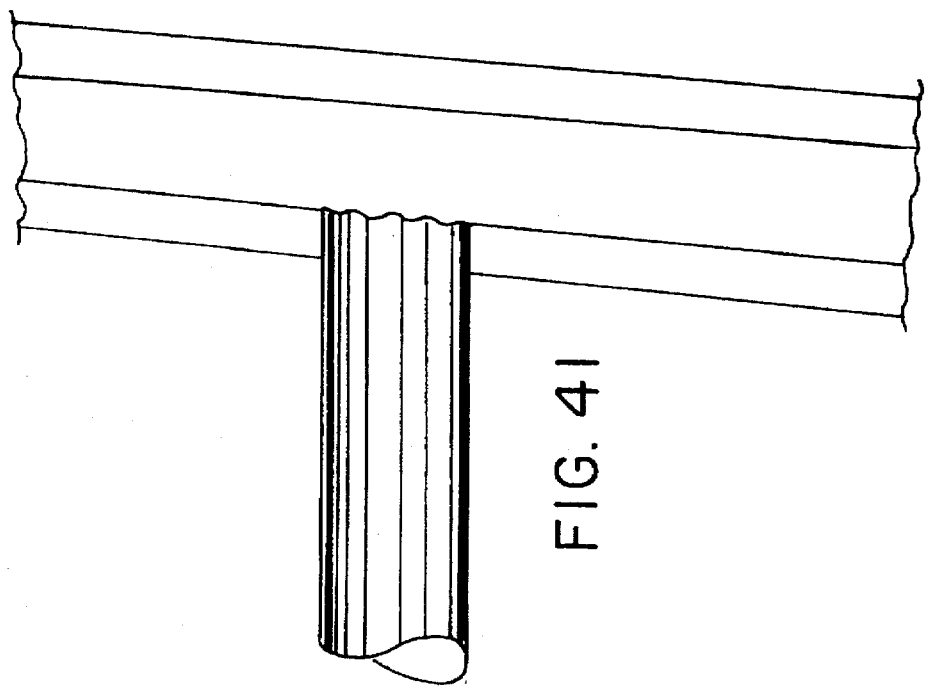
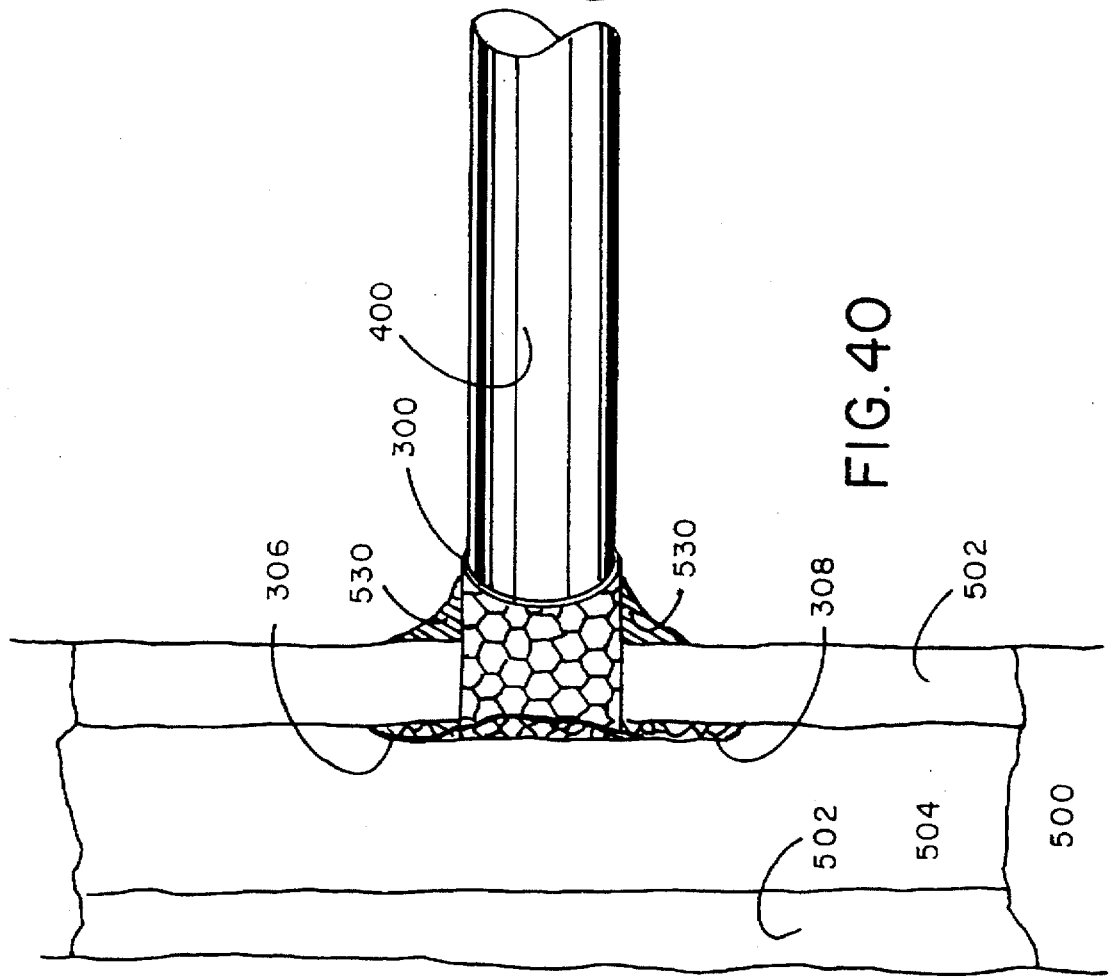

CATHETER APPARATUS AND METHOD FOR CREATING A VASCULAR BYPASS IN-VIVO

FIELD OF THE INVENTION

The present invention is concerned generally with minimally invasive vascular bypass surgery; and is directed to a catheterization methodology for creating a vascular bypass between an unobstructed artery or vein and an obstructed artery or vein in-vivo.

BACKGROUND OF THE INVENTION

Coronary artery disease is the single leading cause of human mortality and is annually responsible for over 900,000 deaths in the United States alone. Additionally, over 3 million Americans suffer chest pain (angina pectoris) because of it. Typically, the coronary artery becomes narrowed over time by the build up of fat, cholesterol and blood clots. This narrowing of the artery is called artherosclerosis; and this condition slows the blood flow to the heart muscle (myocardium) and leads to angina pectoris due to a lack of nutrients and adequate oxygen supply. Sometimes it can also completely stop the blood flow to the heart causing permanent damage to the myocardium, the so-called "heart attack."

The conventional treatment procedures for coronary artery disease vary with the severity of the condition. If the coronary artery disease is mild, it is first treated with diet and exercise. If this first line of treatment is not effective, then the condition is treated with medications. However, even with medications, if chest pain persists (which is usually secondary to development of serious coronary artery disease) the condition is often treated with invasive procedures to improve blood flow to the heart. Currently, there are several types of invasive procedures: (1) Catheterization techniques by which cardiologists use balloon catheters, atherectomy devices or stents to reopen up the blockage of coronary arteries; or (2) Surgical bypass techniques by which surgeons surgically place a graft obtained from a section of artery or vein removed from other parts of the body to bypass the blockage.

Conventionally, before the invasive procedures are begun, coronary artery angiography is usually performed to evaluate the extent and severity of the coronary artery blockages. Cardiologists or radiologists thread a thin catheter through an artery in the leg or arm to engage the coronary arteries. X-ray dye (contrast medium) is then injected into the coronary artery through a portal in the catheter, which makes the coronary arteries visible under X-ray, so that the position and size of the blockages in the coronary arteries can be identified. Each year in U.S.A., more than one million individuals with angina pectoris or heart attack undergo coronary angiographies for evaluation of such coronary artery blockages. Once the blocked arteries are identified, the physician and surgeons then decide upon the best method to treat them.

One of the medically accepted ways to deal with coronary arterial blockage is percutaneous transluminal coronary angioplasty (PTCA). In this procedure, cardiologists thread a balloon catheter into the blocked coronary artery and stretch it by inflating the balloon against the arterial plaques causing vascular blockage. The PTCA procedure immediately improves blood flow in the coronary arteries, relieves angina pectoris, and prevents heart attacks. Approximately 400,000 patients undergo PTCA each year in the U.S. However, when the arterial blockages are severe or widespread, the angioplasty procedure may fail or cannot be performed. In these instances, coronary artery bypass graft (CABG) surgery is then typically performed. In such bypass surgery, surgeons harvest healthy blood vessels from another part of the body and use them as vascular grafts to bypass the blocked coronary arteries. Each vascular graft is attached with one of its ends joined to the aorta and the other end joined to the coronary artery. Approximately 500,000 CABG operations are currently performed in the U.S. each year to relieve symptoms and improve survival from heart attack.

It is useful here to understand in depth what a coronary arterial bypass entails and demands both for the patient and for the cardiac surgeon. In a standard coronary bypass operation, the surgeon must first make a foot-long incision in the chest and split the breast bone of the patient. The operation requires the use of a heart-lung machine that keeps the blood circulating while the heart is being stopped and the surgeon places and attaches the bypass grafts. To stop the heart, the coronary arteries also have to be perfused with a cold potassium solution (cardioplegia). In addition, the body temperature of the patient is lowered by cooling the blood as it circulates through the heart-lung machine in order to preserve the heart and other vital organs.

As the heart is stopped and a heart-lung machine pumps oxygenated blood through the patient's body, the surgeon makes a tiny opening into the front wall of the target coronary artery with a very fine knife (arteriotomy); takes a previously excised saphenous vein (a vein from a leg) or an internal mammary artery (an artery from the chest); and sews the previously excised blood vessel to the coronary artery. The most common blood vessel harvested for use as a graft is the greater (long) saphenous vein, which is a long straight vein running from just inside the ankle bone to the groin. The greater saphenous vein provides a bypass conduit of the most desired size, shape, and length for use with coronary arteries. The other blood vessel frequently used as a bypass graft is the left or right internal mammary artery, which comes off the subclavian artery and runs alongside the undersurface of the breastbone (sternum). Typically, the internal mammary artery remains attached to the subclavian artery proximally (its upper part) but is freed up distally (its lower part); and it is then anastomosed to the coronary artery. However, the saphenous vein graft should be sewn not only to coronary artery but also to the aorta, since the excised vein is detached at both ends. Then, to create the anastomosis at the aorta, the ascending thoracic aorta is first partially clamped using a curved vascular clamp to occlude the proper segment of the ascending aorta; and a hole is then created through the front wall of the aorta to anchor the vein graft with sutures. The graft bypasses the blockage in the coronary artery and restores adequate blood flow to the heart. After completion of the grafting, the patient is taken off of the heart-lung machine and the patient's heart starts beating again. Most of the patients can leave the hospital in about 6 days after the CABG procedure.

It will be noted that coronary artery bypass surgery is considered a more definitive method for treating coronary arterial disease because all kinds of obstructions cannot be treated by angioplasty; and because a recurrence of blockages in the coronary arteries even after angioplasty is not unusual. Also coronary artery bypass surgery usually provides for a longer patency of the grafts and the bypassed coronary arteries in comparison with the results of PTCA procedure. However, coronary artery bypass surgery is a far more complicated procedure, having need of a heart-lung machine and a stoppage of the heart. Also, it is clearly the more invasive procedure and is more expensive to perform than PTCA. Therefore, cardiac surgeons have recently developed an alternative to the standard bypass surgery, namely "minimally invasive bypass operation (MIBO) in order to reduce the risks and the cost associated with CABG surgery. Also, the MIBO is performed without use of a heart-lung machine or the stopping of the heart.

There are several ways that minimally invasive coronary bypass surgeries are being done today. Some versions are modeled after the video-assisted, fiber-optic techniques developed previously for gallbladder and other general surgeries. Other techniques have modified decades-old methods to sew arterial grafts onto beating hearts without using heart-lung machines. In the new and most popular version of the minimally invasive coronary bypass operation, surgeons use a thoracoscope, a fiber-optic device that is similar to a laparoscope. Initially, a three-inch incision is made to the left of the breast bone through which the surgeons operate. Three additional one-inch incisions then are made to insert a video camera, knife, surgical stapler, and other instruments. In the first stage of the operation, surgeons prepare the internal mammary artery, which courses vertically behind the rib cage, while watching on a video monitor. The internal mammary artery is freed up distally and is then sewn to the left anterior descending coronary artery. The internal mammary artery thus supplies blood to the coronary artery in place of blocked circulation of the heart. The wall of the chest formerly served by the mammary artery picks up blood from elsewhere via collateral blood circulations.

As a bypass graft, the left internal mammary artery (LIMA) offers a number of advantages to the coronary artery surgery including higher patency rate; and anatomically, histologically and geometrically provides a more comparable graft than the saphenous vein graft. LIMA is particularly useful as a graft to the coronary arteries such as the left anterior descending, diagonal branches, and ramus intermedius arteries (which are located on the surface of the heart relatively close to the left internal mammary artery). However, there are several disadvantages associated with a CABG operation with a left internal mammary artery graft, which are as follows: (1) technically, this artery is more tedious to take down; (2) sometimes the left internal mammary artery is inadequate in size and length; (3) the operation is suitable only for the five percent of candidates for coronary artery bypass because only a single left internal mammary artery is available as a graft; (4) anatomically, the operation is limited mainly to the left anterior descending coronary artery because of its location ad length; and (5) the majority of patients need more than single vessel bypass surgery.

In comparison, coronary arteries as small as 1 mm in diameter can be revascularized by vein grafting; and the saphenous vein is longer, larger, and more accessible than the left internal mammary artery. Equally important, although the greater or lesser saphenous veins of the leg are preferred, the cephalic or basilic veins in the arm are available as alternatives when the leg veins in the patient are unavailable or are unsuitable. For these reasons, the vein graft has today become the standard conduit for myocardial revascularization.

There remains, however, a long-standing and continuing need for a bypass technique which would allow surgeons to perform multiple bypass procedures using vein grafts as vascular shunts in a minimally invasive way; and, in particular, the need remains for a simpler method to place more than one vein graft proximally to the aorta and distally to the coronary artery without using a heart-lung machine and without stopping the heart. If such a technique were to be created, it would be recognized as a major advance in bypass surgery and be of substantial benefit and advantage for the patient suffering from coronary artery disease.

SUMMARY OF THE INVENTION

The present invention has multiple aspects. A first aspect is a catheter apparatus for creating bypass on-demand between an unobstructed artery and an obstructed artery in-vivo using a previously excised vascular segment as a conduit, said vascular bypass catheter apparatus comprising:

a catheter suitable for introduction into and extension through the body in-vivo, said catheter being comprised of
  (a) a hollow tube of fixed axial length having a discrete proximal end, a discrete distal end, and at least one internal lumen of predetermined diameter, and
  (b) a distal end tip adapted for guidance of said catheter in-vivo to a chosen site wherein an unobstructed artery is in anatomic proximity to an obstruction lying within another artery;

an obturator for on-demand introduction and passage through said catheter to a chosen site on the unobstructed artery in-vivo, said obturator comprising
  (1) an expandable and contractible puncturing headpiece for puncture of and entry into the lumen of an unobstructed artery, said puncturing headpiece being expandable on-demand to a size greater than the diameter of said internal lumen of said catheter and being contractible on-demand to a size less than the diameter of said internal lumen of said catheter,
  (2) a perforating end tip on said puncturing headpiece to facilitate the perforation of an arterial wall at the chosen site in-vivo
  (3) an elongated shaft of fixed axial length integrated with said puncturing headpiece, said elongated shaft being configured for the carrying and transport of the previously excised vascular segment within said internal lumen of said catheter to the chosen vascular site on the unobstructed artery in-vivo,
  (4) means for expanding and contracting said puncturing headpiece of said obturator on-demand; and a deformable cuff for positioning over said elongated shaft adjacent to said puncturing headpiece of said obturator together with a previously excised vascular segment
  (i) wherein, prior to the perforation of the unobstructed artery in-vivo by said puncturing headpiece of said obturator, at least a portion of said deformable cuff has been engaged and joined to one end of the excised vascular segment then carried by said elongated shaft of said obturator,
  (ii) and wherein, after the perforation of the unobstructed artery in-vivo by said puncturing headpiece of said obturator, at least part of said engaged cuff is extended into the lumen of the unobstructed artery, is partially deformed in-situ by an expansion of said puncturing headpiece of said obturator, and said engaged cuff becomes attached via said partial deformation to the interior of the unobstructed artery,
  (iii) and whereby said cuff engaged end of the previously excised vascular segment become secured to and placed in blood flow communication with the unobstructed artery and serves as vascular conduit means for bypassing an obstruction and restoring arterial blood flow from the unobstructed artery to the obstructed artery.

A second aspect of the invention defines a catherization method for creating a vascular bypass on-demand between an unobstructed artery and an obstructed artery in-vivo using a previously excised vascular segment as a conduit, said vascular bypass catheterization method comprising the steps of:

providing a catheter suitable for introduction into and extension through the body in-vivo, said catheter being comprised of
  (a) a hollow tube of fixed axial length having a discrete proximal end, a discrete distal end, and at least one internal lumen of predetermined diameter, and
  (b) a distal end tip adapted for guidance of said catheter in-vivo to a chosen vascular site wherein an unobstructed artery is in anatomic proximity to an obstruction lying within another artery;

providing an obturator for on-demand introduction and passage through said catheter to a chosen site on the unobstructed artery in-vivo, said obturator comprising
  (1) an expandable and contractible puncturing headpiece for puncture of and entry into the lumen of an unobstructed artery, said puncturing headpiece being expandable on-demand to a size greater than the diameter of said internal lumen of said catheter and also being contractible on-demand to a size less than the diameter of said internal lumen of said catheter,
  (2) a perforating end tip on said puncturing headpiece to facilitate the perforation of an arterial wall at the chosen vascular site in-vivo
  (3) an elongated shaft of fixed axial length integrated with said puncturing headpiece, said elongated shaft being configured for the carrying and transport of a previously excised vascular segment within said internal lumen of said catheter to the chosen site on the unobstructed artery in-vivo,
  (4) means for expanding and contracting said puncturing headpiece of said obturator on-demand;

placing a previously excised vascular segment on the elongated shaft adjacent to said puncturing headpiece of said obturator;

positioning a deformable cuff over said elongated shaft and one end of the previously excised vascular segment lying adjacent to said puncturing headpiece of said obturator such that at least a portion of said deformable cuff engages and is joined to the end of the excised vascular segment;

perforating the unobstructed artery at the chosen site in-vivo using said puncturing headpiece of said obturator;

extending at least part of said engaged cuff into the lumen of the unobstructed artery;

partially deforming said extended cuff in-situ by an expansion of said puncturing headpiece of said obturator
  (i) whereby said engaged cuff becomes attached via said partial deformation to the interior of the unobstructed artery,
  (ii) and whereby said cuff engaged end of the previously excised vascular segment become secured to and placed in blood flow communication with the unobstructed artery; and joining the other end of the secured vascular segment to the obstructed artery at a chosen site distal to the obstruction, said joined segment serving as a vascular conduit means for bypassing the obstruction and restoring arterial blood flow from the unobstructed artery to the obstructed artery.

BRIEF DESCRIPTION OF THE FIGURES

The present invention may be more easily and completely understood when taken in conjunction with the accompanying drawing, in which:

FIGS. 3A and 3B are perspective and cross-sectional views of a single wall catheter tube of normal thickness;

FIGS. 4A and 4B are perspective and cross-sectional views of a single wall catheter tube of reduced thickness;

FIGS. 5A and 5B are perspective and cross-sectional views of a multiple-wall catheter tube of normal thickness;

FIGS. 6A and 6B are perspective and cross-sectional views of a multiple-wall catheter tube of reduced thickness;

FIG. 9 is a perspective view of a preferred first obturator;

FIG. 10 is a frontal view of the first obturator of FIG. 9;

FIG. 11 is a side view of the puncturing headpiece of the first obturator shown in FIG. 9;

FIG. 12 is a side view of the puncturing headpiece of FIG. 11 when in a contracted state;

FIG. 13 is a side view of the puncturing headpiece of FIG. 11 when in an expanded state;

FIG. 18 is a perspective view of a third obturator;

FIG. 19 is a frontal view of the third obturator of FIG. 18;

FIG. 28 is a perspective view of a previously excised vascular segment position on the elongated shaft of the preferred first obturator of FIG. 9;

FIG. 29 is a perspective view of the preferred first deformable cuff of FIG. 23 in combination with the previously excised vascular segment shown in FIG. 28;

FIG. 34 is a partially exposed view of the prepared obturator entering the internal lumen of the unobstructed blood vessel in-vivo;

FIG. 35 is a partially exposed view of the puncturing headpiece in a contracted state while disposed within the internal lumen of the unobstructed blood vessel in-vivo;

FIG. 36 is a partially exposed view of the deformable cuff and engaged over the puncturing headpiece within the internal lumen of the unobstructed blood vessel in-vivo;

FIG. 37 is a partially exposed view of the subsequently expanded puncturing headpiece and the deformed cuff disposed within the internal lumen of the unobstructed blood vessel in-vivo;

FIG. 38 is a partially exposed view of the puncturing headpiece in the secondary contracted state after deformation of the cuff within the internal lumen of the unobstructed blood vessel in-vivo;

FIG. 39 is a partially exposed view of the deformed cuff and vascular segment secured fluid-tight to and in blood flow communication with the internal lumen of the unobstructed blood vessel in-vivo;

FIG. 40 is a partially exposed view of the vascular bypass grafted and secured to the unobstructed blood vessel in-vivo; and FIG. 41 is a partially exposed view of the other open end of the vascular segment anastomosed in the conventionally known manner to an obstructed blood vessel.

DETAILED DESCRIPTION OF THE INVENTION

Figure 1:
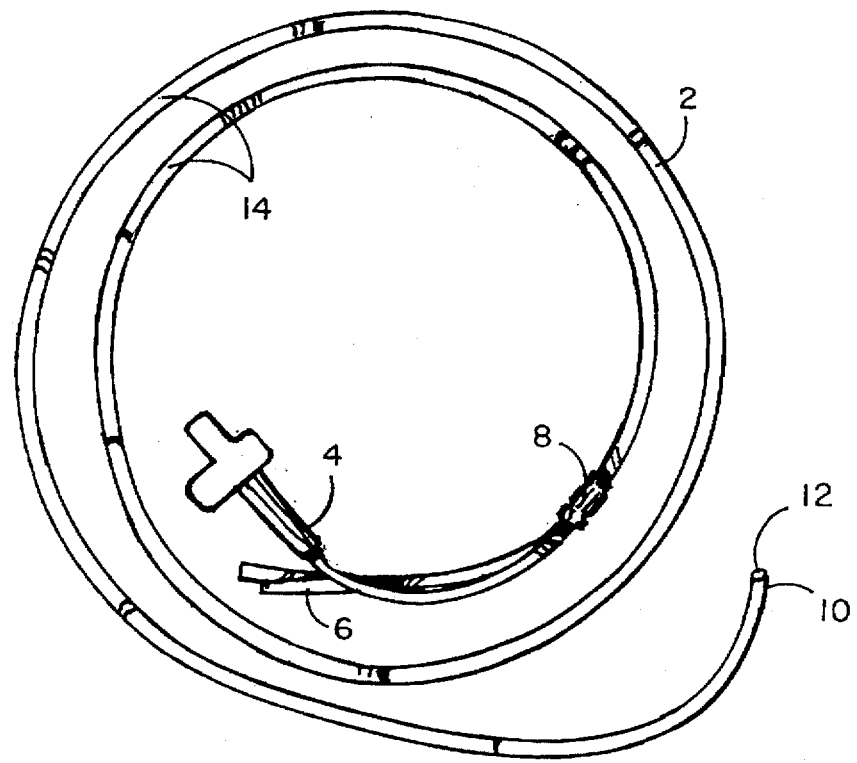
FIG. 1 is an overhead view of a conventionally known first catheter.

The present invention is a catheter apparatus and catherization technique for creating a single vascular bypass or multiple vascular bypasses on-demand between an unobstructed blood vessel such as the aorta and an obstructed blood vessel such as an obstructed coronary artery in-vivo. The present invention utilizes a previously excised vascular segment as a conduit; and employs an introducer system using the catheter apparatus and excised vascularl segment in combination to create single or multiple shunts which overcome the obstruction and deliver arterial blood from a primary blood vessel, around the obstruction and into a secondary artery or vein in order to increase and/or maintain proper blood circulation in the living body. A number of substantial advantages and major benefits are therefore provided by the present invention, some of which include the following:

1. The present invention provides the means for surgeons to perform multiple bypass grafts in a minimally invasive manner. The methodology permits the surgeon to utilize previously excised veins as bypass grafts; and allows the surgeon to place each of the vein grafts from a primary unobstructed artery (such as the aorta) to a secondary obstructed artery (such as the obstructed coronary artery) without using a heart-lung machine and without need for stopping the heart during the surgery.

2. The present invention simplifies the complexity of conventional bypass surgery and makes the surgery less invasive. Moreover, the technique provides the ability to create multiple bypass conduits using a catheterization procedure which not only shortens the conventional operation time for surgery but also makes the bypass surgery safer and more cost effective.

3. The present invention is suitable for creating a single bypass graft or multiple bypass grafts in any medical situation, condition, or pathology in which there is a need for increased blood flow to a specific blood vessel or vascular area or body region. The cause or source of the medical problem may be an obstruction in a blood vessel; or a narrowing or thickening of a blood vessel wall; or a diminution or narrowing of a vascular section in a particular blood vessel. Each of these medical conditions has its particular cause, origin, or source; and each of these pathologies, though different in origin, causes a similar effect overall—a loss of blood flow and blood pressure within the blood vessel. Accordingly, the present invention is deemed useful and desirable to overcome any of these particular medical conditions and instances where there is a demonstrated need for increased blood pressure and blood volume flow within a particular blood vessel or blood flow region in the body.

4. The present apparatus and methodology can be employed to create a vascular bypass between any two blood vessels. In many instances, the vascular bypass graft is made between a primary unobstructed artery and a secondary obstructed artery, a typical example being a vascular bypass between the ascending aorta and an obstructed coronary artery. However, a vascular bypass shunt may also be created between any two veins (such as between the portal vein and the inferior vena cava); or between an artery and a vein (such as between the superior vena cava and a pulmonary artery). Equally important, although the primary focus of the present invention is the thoracic cavity and the recognized need for vascular bypass conduits among the blood vessels found therein, the present apparatus and methodology may be employed anywhere in the human body where there is a need for increased vascularization or revascularization of the local region. The sole limitation, therefore, is a means of access for the catheter apparatus, the introducer system, and the methodology to be performed by the skilled surgeon and invasive radiologist.

In order to provide a complete and comprehensive understanding of the present invention, the detailed description is given as a series of individual sections presented seriatim. These will include the following: the component parts of the catheter apparatus; the excised blood vessel segment to be used as a vascular conduit; the introducer system utilizing the catheter apparatus and excised vascular segment in combination; general techniques of catheter routing and surgical introduction; the methodology and individual manipulations for creating a vascular graft; and an illustrative summary of the preferred surgical procedures using the catheter apparatus, introducer system, and methodology. Each of these will be described and characterized individually.

I. The Component Parts of the Catheter Apparatus

Three essential component parts comprise the catheter apparatus needed to create a vascular bypass in-vivo. These are: a flexible guiding catheter; an obturator having a puncturing headpiece which is expandable and contractible on-demand; and a deformable cuff for engaging and securing a previously excised vascularl segment as a graft to an unobstructed major blood vessel (such as the aorta). Each of these component parts will be described in detail individually.

A. The Flexible Guiding Catheter

The in-vivo bypass catheterization method comprising the present invention requires that a controlling or guiding flexible catheter be employed as an essential part of the apparatus and manipulations. This controlling or guiding flexible catheter has at least one tubular wall of fixed axial length; has at least one proximal end for entry; has at least one distal end for egress; and has at least one internal lumen of a volume sufficient to allow for on-demand controlled passage therethrough of a prepared obturator carrying a cuff and a previously excised vascular segment.

Catheters, particularly surgical catheters, are conventionally known and used; and a wide range and variety of guiding catheters are available which are extremely diverse in shape, design, and specific features. All of the essential requirements of a guiding flexible catheter exist as conventional knowledge and information in the relevant technical field; and all of the information regarding catheter design and provided in summary form hereinafter is publicly known, widely disseminated, and published in a variety of authoritative texts. The reader is therefore presumed to be both familiar with and have an in-depth knowledge and understanding of the conventional diagnostic and therapeutic uses of catheters and cathertization techniques. Merely representative of the diversity of publications publicly available are the following, each of which is expressly incorporated by reference herein: *Diagnostic and Therapeutic Cardiac Cathertization*, second edition (Pepine, Hill, and Lambert, editors) Williams & Wilkins, 1994 and the references cited therein; *A Practical Guide To Cardiac Pacing*, fourth edition (Moses et. al., editors) Little, Brown, and Company, 1995 and the references cited therein; *Abrams Angiography*, third edition (H. L. Abrams, editor), Little, Brown, and Company, 1983.

A number of specific types of controlling or guiding catheters are known today; but for purposes of practicing the present invention, a number of newly designed or specifically designed catheters of varying lengths and sizes suitable for bypass use are expected and intended to be developed and manufactured subsequently. Equally important, minor modifications of the presently existing general categories of catheters are equally appropriate and are expected to be found suitable for use when practicing the present invention. Accordingly, a summary review of the conventionally known catheter types as well as a summary description of general catheter design and the principles of catheter construction are presented herein.

Catheter Construction and Design:

Presently known specific types of catheters include the following: central venous catheters which are relatively short (usually 20–60 centimeters) in length and are designed for insertion into the internal jugular or subclavian vein; right heart catheters such as the Cournard catheter designed specifically for right heart catheterization; transseptal catheters developed specifically for crossing from right to left atrium through the interarterial septum at the fossa ovalis; angiographic catheters which are varied in shape and are frequently used today in the femorial and brachial approach for cardiac catheterization and angiography in any of the major vessels; coronary angiographic catheters which include the different series of grouping including Sones, Judkins, Amplatz, multipurpose, and bypass graft catheters; as well as many others developed for specific purposes and medical conditions.

Figure 2:
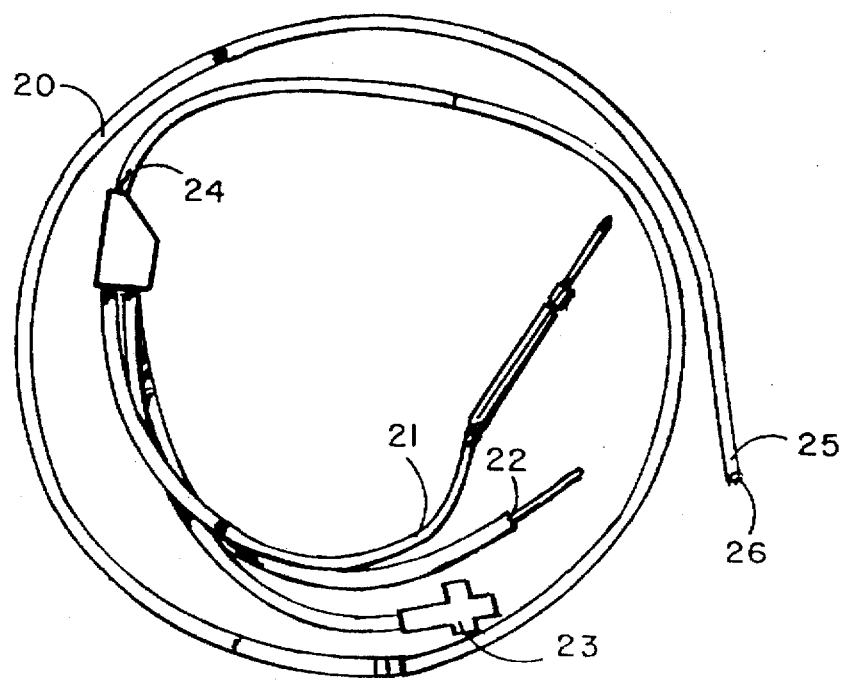
FIG. 2 is an overhead view of a conventionally known second catheter.

Merely representative of guiding and controlling flexible catheters, generally presented herein without regard to their specific past usages or intended applications, are those illustrated by FIGS. 1 and 2 respectively. As exemplified by the catheter of FIG. 1, a catheter 2 is seen having a tubular wall of fixed axial length; having two proximal portals 4 and 6 which together generate the proximal end 8 for entry into the interior of the catheter; a single distal portal 10 and the distal end 12 of the catheter; and an internal lumen 14 (which is not visible in the illustration).

Another variation commonly known is illustrated by FIG. 2 which shows a controlling flexible catheter 20 having a tubular wall of fixed axial length; three proximal portals 21, 22 and 23 respectively which collectively form the proximal end 24 for entry into the internal volume of the catheter; and a single distal portal 25 which designates the distal end 26 or tip of the catheter. It will be appreciated and understood that FIGS. 1 and 2 are presented merely to show the overall general construction and relationship of parts present in each flexible controlling catheter suitable for use with the present methodology.

In accordance with established principles of conventional catheter construction, the axial length of the catheter may be composed of one or several layers in combination. In most multilayered constructions, one hollow tube is stretched over another to form a bond; and the components of the individual layers determine the overall characteristics for the catheter as a unitary construction. Most multilayered catheters comprise an inner tube of teflon, over which is another layer of nylon, woven Dacron, or stainless steel braiding. A tube of polyethylene or polyurethane is then heated and extruded over the two inner layers to form a bond as the third external layer. Other catheter constructions may consist of a polyurethane inner core, covered by a layer of stainless steel braiding, and a third external jacket layer formed of polyurethane.

Several examples of basic catheter construction and design are illustrated by FIGS. 3–6 respectively. FIGS. 3A and 3B are perspective and cross-sectional views of a single tubular wall considered the standard minimum construction for a catheter. FIGS. 4A and 4B are perspective and cross-sectional views of a thin-walled design for a single layer extruded catheter. In comparison, FIGS. 5A and 5B are perspective and cross-sectional views of a standard multilayered catheter construction having a braided stainless steel midlayer in its construction. Finally, FIGS. 6A and 6B are perspective and cross-sectional views of a thin-walled design for a multilayered catheter with a braided stainless steel middle layer.

Catheters are generally sized by external and internal diameter and length. The internal specified either by diameter (in thousandths of an inch or millimeters or French). Many newer thin-walled catheter designs provide a much larger internal lumen volume to external diameter ratio than has been previously achieved, this has resulted in catheters which can accommodate much more volume and allow the passage of much larger sized articles through the internal lumen. External diameter is typically expressed in French sizes which are obtained by multiplying the actual diameter of the catheter in millimeters by a factor of 3.0. Conversely, by traditional habit, the size of any catheter in millimeters may be calculated by dividing its French size by a factor of 3.0. French sizes from 5–8 are currently used for diagnostic angiography. For purposes of practicing the present invention, it is also desirable that French sizes ranging from 4–16 respectively be employed unless other specific size requirements are indicated by the particular application or circumstances. In addition, because of the variation between standard, thin-walled, and super high-flow catheter construction designs, a range and variety of external and internal lumen diameter sizes exist. To demonstrate the conventional practice, the data of Table 1 is provided.

TABLE 1

External and Lumen Diameter Measurements in Standard, Thin-Walled, and Super High-Flow Diagnostic Catheters

| French Size | External Diameter | | Internal Diameter | | | | | |
|---|---|---|---|---|---|---|---|---|
| | | | Standard (High Torque) | | Thin-Walled (High Flow) | | Super (High Flow) | |
| | inches | mm | inches | mm | inches | mm | inches | mm |
| 5 | 0.065 | 1.67 | a | a | 0.044 | 1.08 | 0.052 | 1.28 |
| 6 | 0.078 | 2.00 | a | a | 0.050 | 1.27 | 0.056 | 1.42 |
| 7 | 0.092 | 2.34 | 0.048 | 1.22 | 0.056 | 1.42 | 0.061 | 1.55 |
| 8 | 0.104 | 2.64 | 0.056 | 1.42 | 0.063 | 1.60 | a | a |
| 9 | 0.118 | 3.00 | a | a | a | a | a | a | aNo catheters made in this size/type.

Dual-lumen catheters:

A number of different dual-lumen catheters are known today which differ in the size and spatial relationship between their individual lumens. This is illustrated by FIGS. 7A–7D respectively which show different dual-lumen constructions for four catheters having similar or identical overall diameter (French) size.

Figure 7A:
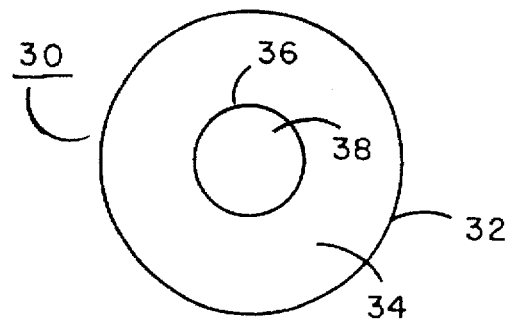
FIGS. 7A–7D are cross-sectional views of four different constructions of dual-lumen catheters.

As shown therein, FIG. 7A shows a dual-lumen catheter 30 wherein a first external tubular wall 32 provides an outer lumen volume 34 into which a second internal tubular wall 36 has been co-axially positioned to provide an inner lumen volume 38. Clearly, the construction of catheter 30 is a co-axial design of multiple tubular walls spaced apart and co-axially spaced but separate internal lumens of differing individual volumes.

Figure 7B:
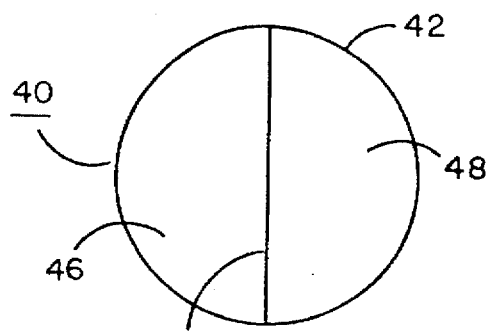

In comparison, FIG. 7B shows a second kind of construction and design by dual-lumen catheter 40 having a single external tubular wall 42; and an centrally disposed inner septum 44 which divides the interior tubular space into two approximately equally lumen volumes 46 and 48 respectively. Thus, in this construction, the diameter, length, and volume of internal lumen 46 is effectively identical to the diameter, length and volume of internal lumen 40; and both of these exist and are contained within a single, commonly-shared, tubular wall.

Figure 7C:
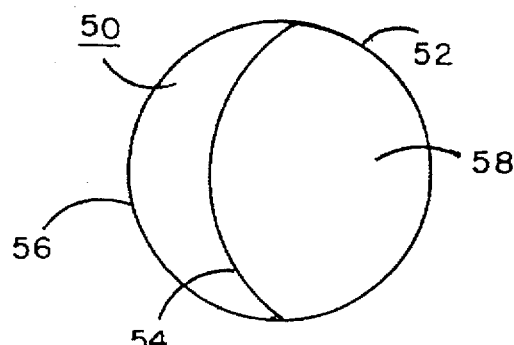

A third kind of construction is illustrated by FIG. 7C and shows an alternative kind of construction and design to FIG. 15B. As seen in FIG. 7C, dual-lumen catheter 50 has a single external tubular wall 52; and contains an asymmetrically positioned internal divider 54 which divides the interior tubular space into two unequal and different lumen volumes 56 and 58 respectively. Thus, in this alternative construction, the discrete volume of internal lumen 56 is markedly smaller than the volume of the adjacently positioned internal lumen 58; and yet both of these internal lumens 56 and 58 exist in, are adjacently positioned, and are both contained within a commonly-shared single tubular wall.

Figure 7D:
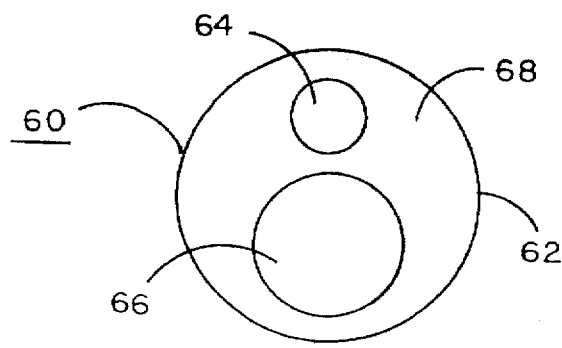

A fourth construction and design for a dual-lumen catheter is presented by FIG. 7D which shows a catheter 60 having a single external tubular wall 62 of relatively large size and thickness. Within the material substance 68 of the tubular wall 60 are two discrete bore holes 64 and 66 of differing diameters which serve as two internal lumens of unequal volume. Internal lumen 64 is clearly the smaller while internal lumen 66 is far greater in spatial volume. Yet each internal lumen volume 64 and 66 is adjacent to the other, lies in parallel, and follows the other over the axial length of the catheter.

Figure 8:
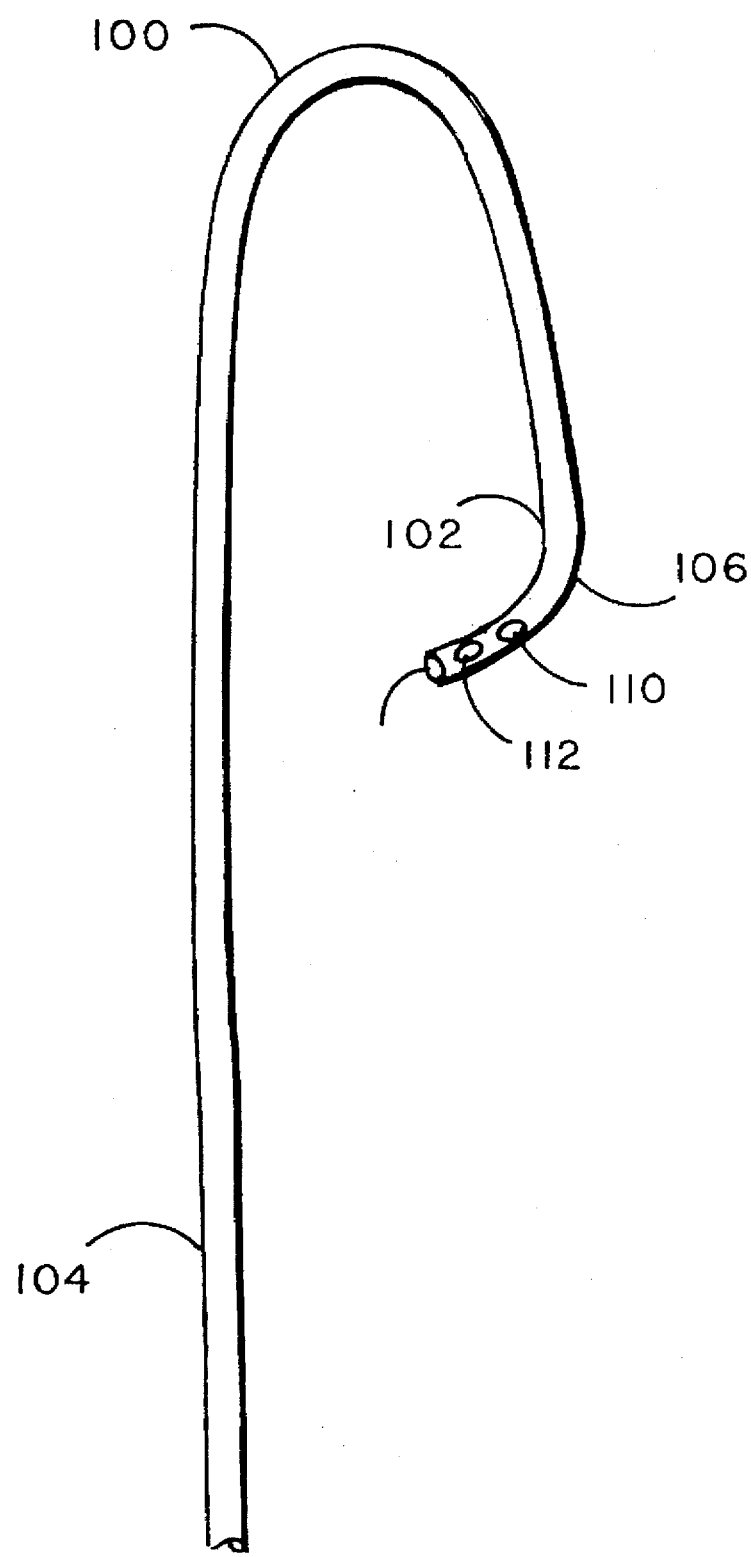
FIG. 8 is an illustration of the distal end of a conventionally known guiding catheter.

In general, the tubular body of the catheter is generally straight over most of its length and may have different bends or curves towards the distal end or tip. A representative illustration of the distal end of a catheter is illustrated by FIG. 8. The individual bends in the catheter are traditionally called "curves"; and the terms "primary, secondary, etc.," are applied to each additional curve further away from the distal tip as is illustrated by FIG. 8. Accordingly, the primary curve 100 is followed by the secondary curve 102, which in turn extends into the catheter body 104 generally. The catheter tip 106 is its most distal segment. In addition, the catheter distal tip 106 may have any combination of a single end hole 110 or an open distal end 108 and any number of side holes 110, 112 which function as portals for fluids and gases exiting the distal end of the catheter.

Conventional practice permits a number of different distal ends or tips which vary in design and appearance. Merely representative of these permitted and conventional variances in distal end design for catheters generally are the distal ends of ventricular catheters which include: a "pigtail" design and construction which has a curled-tip format and multiple side holes; the Lehman ventricular catheter end which provides a number of side holes in different places along the distal end; and the Gensini design which provides multiple side holes at varying angles. Accordingly, for purposes of practicing the present repair methodology, any construction of the catheter distal end whether having one or more curves, or none; and whether or not there is more than one central portal for exiting the lumen or multiple side holes, are all considered conventional variations in construction design. Any and all of these distal tip designs and constructions are therefore deemed to be encompassed completely and to lie within the general catheter scope of construction suitable for use with the present invention.

B. The Obturator

The second requisite component part of the catheter apparatus is the obturator. Each embodiment of an obturator preferably comprises four parts: a puncturing headpiece; a perforating end tip on the headpiece; an elongated shaft integral with the puncturing headpiece; and means for expanding and contracting the size of the puncturing headpiece on-demand. Various embodiments representative of each of these structural components are individually illustrated within FIGS. 9–15 respectively.

One preferred embodiment of an obturator is illustrated by FIGS. 9–13 respectively. As seen therein, the obturator 120 comprises a puncturing headpiece 122 which is substantially cone-shaped in configuration, and comprises an outer shell 124 and a base plate 126. The outer shell 124 has determinable dimensions and a girth which can be altered in size. At the distal end 128 of the puncturing headpiece 122 is a perforating end tip 130 which appears as a cross- or star-shaped cutting edge for the headpiece 122. As shown by FIG. 10, the perforating end tip 130 does not extend over the entire surface area of the outer shell 124; instead, the perforating end tip 130 is limited in size and orientation to the distal end 128. The perforating end tip 130 serves as the sharp cutting edge for the obturator 120 as a whole.

Integral with the puncturing headpiece 122 is an elongated shaft 134 whose overall axial length may be varied to accommodate the surgeon and the particular medical circumstances of usage. The distal end 136 of the shaft is integrated with the puncturing headpiece 122 and provides access to the interior volume of the headpiece bounded by the outer shell 124 and the base plate 126. The proximal end 138 of the elongated shaft 134 is intended to be held by the surgeon or invasive radiologist performing the vascular bypass surgery. Accordingly, the axial length of the elongated shaft 134 will vary and accommodate the surgeon; and thus vary from a few inches to a few feet in length. The function of the elongated shaft 134 is for the carrying and transport of a previously excised vascular segment to the chosen site on the unobstructed or primary blood vessel in-vivo. The elongated shaft 134 acts to support, maintain and convey the excised vascular segment within the lumen of the catheter in a manner such that the vascular segment can be used as a bypass graft.

A critical requirement and feature of the puncturing headpiece 122 and the obturator 120 as a whole is that means exist for expanding and contracting the puncturing headpiece on-demand. This requirement and characteristic is illustrated by FIGS. 11–13 respectively. As seen within FIG. 11, the puncturing headpiece 122 appears in its initial size identical to that shown by FIG. 9. The outer shell 124 is substantially cone-shaped in configuration, has an initial internal volume, and has a girth dimension d equal to the initial diameter of the base plate 126. The internal volume of the puncturing headpiece, as determined by the dimensions of the outer shell 124 and the base plate 126, provides an initial internal volume of determinable quantity.

When the mechanism for contracting the puncturing headpiece is activated, the consequence is illustrated by FIG. 12 in which the dimensions of the outer shell 124 are diminished and the girth of the headpiece has been reduced as shown by the reduced diameter d' of the base plate 126. Note also, that as the puncturing headpiece 122 becomes contracted in overall volume and dimensions, the configuration of the puncturing headpiece 122 has consequentially become altered and now appears to be spear-like in configuration. Similarly, the overall angular disposition of the perforating end tip 130 serving as the cutting edge will also be slightly altered in overall appearance as a consequence of contracting the puncturing headpiece 122.

Alternatively, when the puncturing headpiece 122 is expanded, the overall result is shown by FIG. 13. As seen therein, the outer shell 124 has been expanded in overall dimensions and volume; and the girth of the headpiece has been expanded and can be determined by the diameter d" of the expanded base plate 126. Note that the overall appearance of the puncturing headpiece has been altered as a consequence of its expansion and now appears to be elliptical in shape overall. Similarly, the perforating end tip 130 has similarly been altered in appearance and has angularly expanded somewhat to conform with the expanded dimensions and angularity of the outer shell 124.

It will be recognized and appreciated also that throughout the changes in appearance, internal volume and overall size for the contracted or expanded puncturing headpiece 122 as shown via FIGS. 11, 12, and 13 respectively, the dimensions and overall configuration of the elongated shaft 134 have not been altered meaningfully or significantly. Although this is not an absolute requirement in each and every embodiment of an obturator, it is preferred that the elongated shaft 134, particularly at the integrated distal end 136, remain constant in size and volume as much as possible and be unaffected subsequent to the on-demand expansion or contraction of the puncturing headpiece 122. This preference and feature will maintain the integrity and continued viability of the excised vascular segment intended to be carried and transported by the elongated shaft during the bypass grafting procedure. Thus, to avoid or minimize any physical damage to the vascular wall of the graft material, it is most desirable that the elongated shaft be maintained in appearance, configuration and dimensions without change whenever possible.

An essential feature and component of each obturator is the existence and availability of specific means for expanding and contracting the puncturing headpiece on-demand. A number of different mechanisms and means for expanding and contracting the puncturing headpiece of the obturator are conventionally known and easily employed. Merely to demonstrate some different and conventionally known mechanisms, attention is directed to the means illustrated by FIGS. 14 and 15 respectively.

Figure 14:
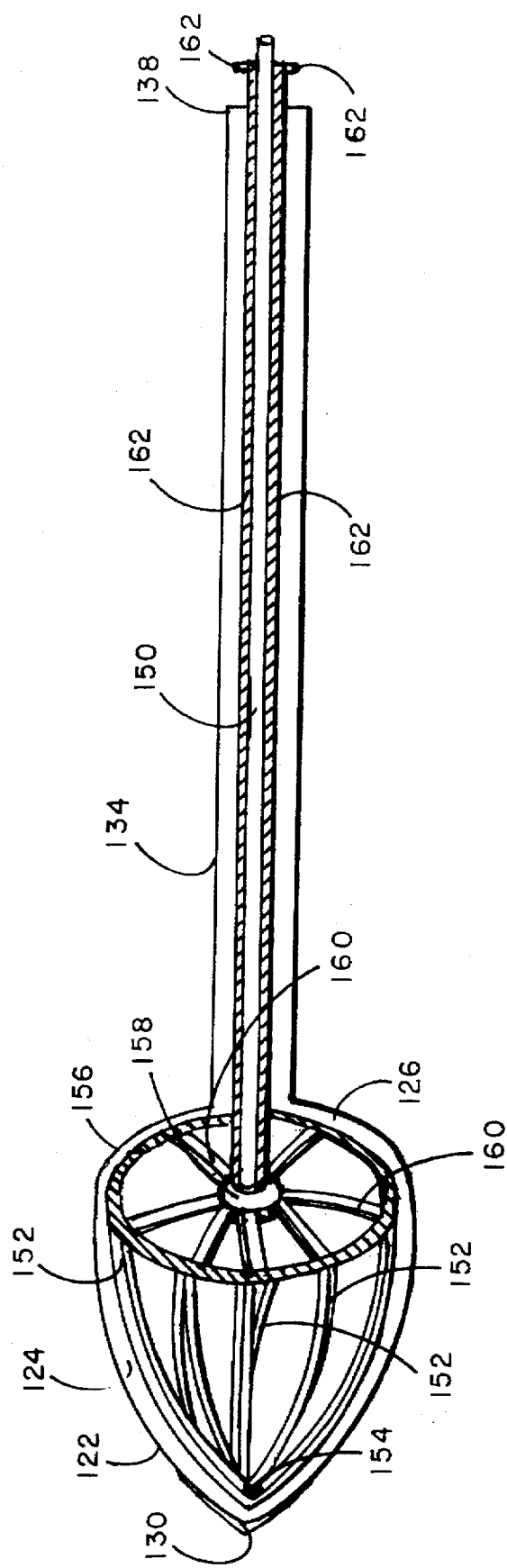
FIG. 14 is an exposed view of a mechanical assembly used for expanding and contracting a puncturing headpiece on-demand in an obturator.

The means for expanding and contracting the puncturing headpiece on-demand illustrated by FIG. 14 constitute a mechanical approach and design mechanism which is carried within the internal volume of the puncturing headpiece 122 and the integrated elongated shaft 134. As seen therein, a central rod 150 extends through the hollow interior of the elongated shaft 134 and extends into the internal volume defined by the outer shell 124 and the base plate 126 of the puncturing headpiece 122. Within the internal volume of the outer shell 124, a plurality of rotable ribs 152 are joined to the central rod 150 at the distal end to form a central pivot point 154. Each rotable rib 152 is mobile and pivotable around the central point 154 and forms an umbrella-like scaffolding structure which can be expanded outwardly or collapsed inwardly at will. Mounted on the central rod 150 is an expansion wheel 156. This expansion wheel 156 is centrally mounted on the rod 150; is moveable over the axial length of the central rod 150; and is controlled in the direction of axial movement (distally and proximally). The expansion wheel 156 comprises a center hub 158 and a plurality of hub supports 160, both of which maintain the expansion wheel in proper position as it engages the plurality of rotable ribs 152. Joined to the central hub 158 of the expansion wheel 156 are linear movement members 162 which are positioned within the interior volume of the elongated shaft 134 and have a length sufficient to reach to the proximal end 138 of the elongated shaft 134 for control by the surgeon or invasive radiologist. The linear movement members 162 engage the center hub 158 of the expansion wheel 156; and extend or withdraw the expansion wheel closer to or away from the perforating end tip 130 of the puncturing headpiece 122. When the expansion wheel is engaged and pushed forward, expansion wheel engages the rotable ribs 152 and expands the rotable ribs outwardly thereby increasing the overall girth of the puncturing headpiece as a unit. Alternatively, when the linear movement members 162 are withdrawn, the expansion wheel recedes towards the proximal end and the engaged rotable ribs 152 collapse inwardly within the volume of the outer shell 124. The consequence of this movement is a contraction of the puncturing headpiece 122 as a unit. It will be recognized and appreciated that this mechanical approach for expanding and contracting the puncturing headpiece is completely conventional in design and operation; and accordingly, any conventional refinement of these basic component parts is considered to be a variation within the scope of this mechanical system.

Figure 15:
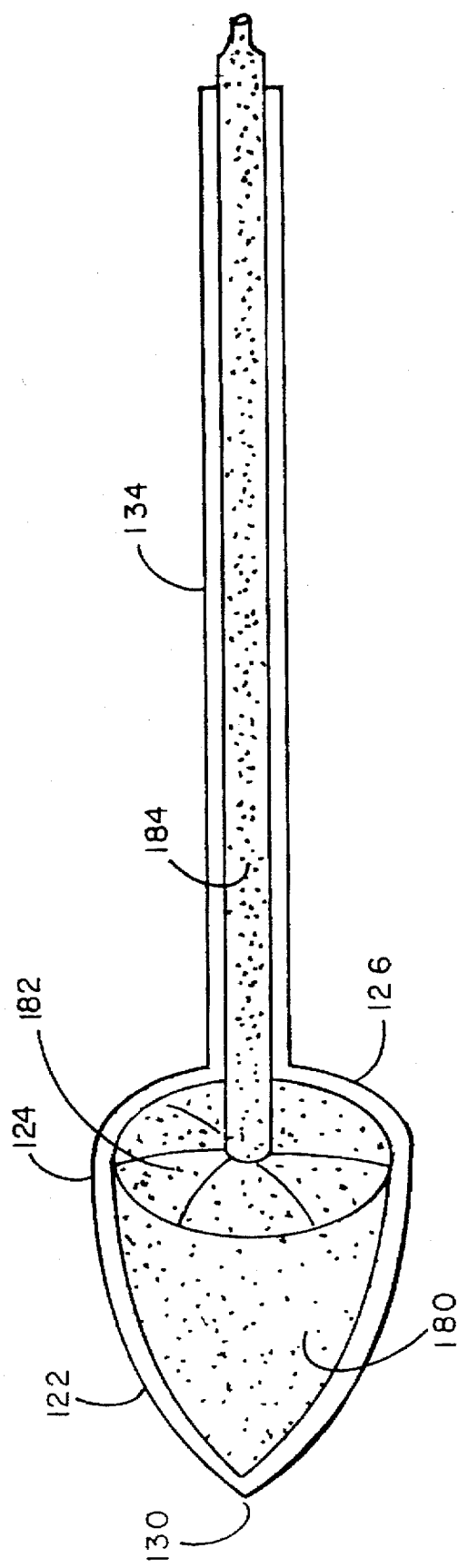
FIG. 15 is an exposed view of a hydraulic assembly for expanding and contracting a puncturing headpiece on-demand in an obturator.

As a representated alternative, hydraulic means for expanding and contracting the puncturing headpiece of the obturator on demand is also provided. In this system, as shown by FIG. 15, the internal volume of the puncturing headpiece 122 and the integrated elongated shaft 134 includes an elastic sack 180 comprised of a fluid containing elastic bubble 182 and a fluid delivering elastic conduit 184. The outer shell 124 and base plate 126 of the puncturing headpiece 122 are as previously shown; and the headpiece 122 is integrated with the elongated shaft 134 as previously described herein. Within the internal volume of the puncturing headpiece 122, is a fluid containing elastic bubble 182 which is in fluid communication with the elastic conduit 184 carried within the internal volume of the elongated shaft 134. The elastic sack 180 is formed of elastomeric material (such as rubber, elastic plastic, and the like) and is fluid-tight along its seams. The elastic sack 180 contains any liquid which is compatible with the material of the elastic sack; and it is the intrinsic nature of the material forming the elastic sack 180 that the material exerts a compression force or pressure upon the fluid contained within the elastic sack itself. In this way a hydraulic system for expanding and contracting the puncturing headpiece of the obturator is created.

As fluid is introduced through the elastic conduit 180 by the surgeon or invasive radiologist, that fluid is conveyed and delivered into the elastic bubble 182 positioned within the puncturing headpiece 122. The elasticity of the bubble 182 exerts a mild compression force and pressure against the quantity of fluid contained within the bubble interior volume; accordingly, the greater the quantity of fluid within the elastic bubble 182, the larger in overall volume the elastic bubble becomes. Thus, as more fluid is delivered through the conduit 184 into the elastic bubble 182, the larger in overall volume the elastic bubble becomes; and as the volume of the elastic bubble expands, the overall configuration and internal volume of the piercing headpiece 122 also enlarges. In this manner, by carefully controlling the amount of fluid conveyed through the conduit 184 into the elastic bubble, the overall size and configuration of the piercing headpiece 122 can be controllably expanded. Subsequently, to reduce the overall size and configuration of the puncturing headpiece 122, a quantity of fluid is permitted to be released from the elastic conduit 184 at the proximal end by the surgeon or radiologist. Because the material is elastic and exerts a compression force against the quantity of fluid present within the bubble at any given moment in time, the release of fluid through the elastic conduit will cause a reduction in overall size for the elastic bubble 182; and as the overall volume of the elastic bubble is reduced in size, the puncturing headpiece will consequently be contracted and reduced in configuration and overall volume as well. It will be noted and appreciated also that this hydraulic mechanism for expanding and contracting the puncturing headpiece on demand is a conventionally known fluid system and technique; and many conventionally known variations and changes in hydraulic design and fluid control systems are presently known and commonly available for use. Accordingly, all hydraulic systems are envisioned as suitable for use as one means for expanding and contracting the puncturing headpiece of the obturator on-demand.

A number of different physical embodiments for the obturator are also envisioned and intended for use. Some examples, which are merely illustrative of the range and variety of physical formats and which serve to merely illustrate the range and degree of difference available for the various puncturing headpieces of an obturator, are illustrated by FIGS. 16–22 respectively. It will be recognized and understood, however, that these alternative embodiments are merely representative and illustrative of obturators and puncturing headpieces generally and do not signify any limitation or restriction on their structural construction or design.

Figure 16:
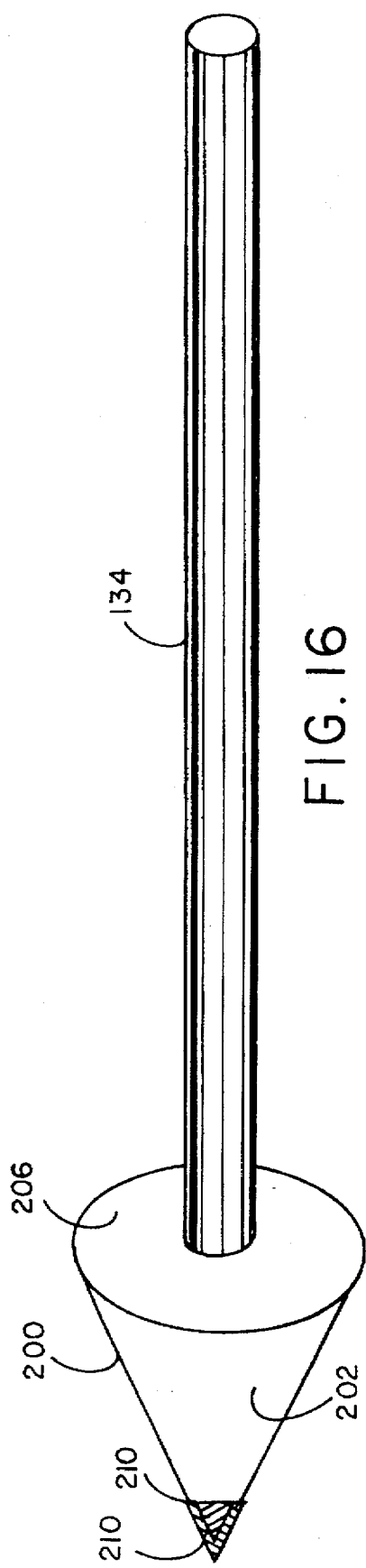
FIG. 16 is a perspective view of a second obturator.
Figure 17:
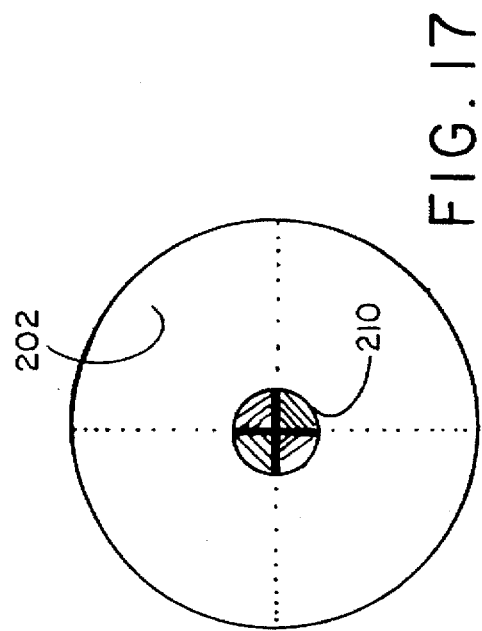
FIG. 17 is a frontal view of the second obturator of FIG. 16.

The embodiment illustrated by FIGS. 16 and 17 respectively shows a puncturing headpiece 200 which is substantially cone-shaped in overall appearance and comprises an outer shell 202 and a base plate 206. The distal end 208 of the puncturing headpiece 200 has a perforating end tip 210 which is also substantially cone-shaped in configuration and appearance and covers only a small surface area of the outer shell 202. Integral with the puncturing headpiece is the elongated shaft 134 as described previously herein; and means for expanding and contracting the puncturing headpiece 200 on-demand are included within the obturator as a integrated unit.

Another embodiment for the puncturing headpiece is illustrated by FIGS. 18 and 19 respectively. As shown therein, the puncturing headpiece 220 comprises the outer shell 222 and the base plate 224 integral with the elongated shaft 134. A particular feature of this embodiment, however, is the distal end 226 seen most clearly within FIG. 19 as providing a perforating end tip 230 which is substantially star-shaped and extends over the surface area of the outer shell 222. The result is to provide a series of grooves 228 alternating with sharp cutting edges 232 over the surface of the outer shell 222. This embodiment for the puncturing headpiece 220 provides a much greater area for cutting and perforation as a specific feature of the obturator design.

Figure 20:
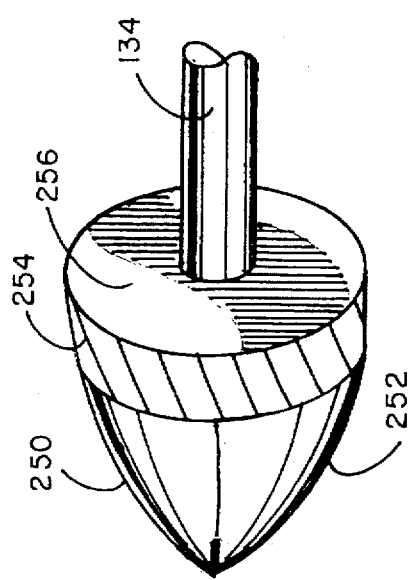
FIG. 20 is a side view of an alternative fourth puncturing headpiece of an obturator.
Figure 21:
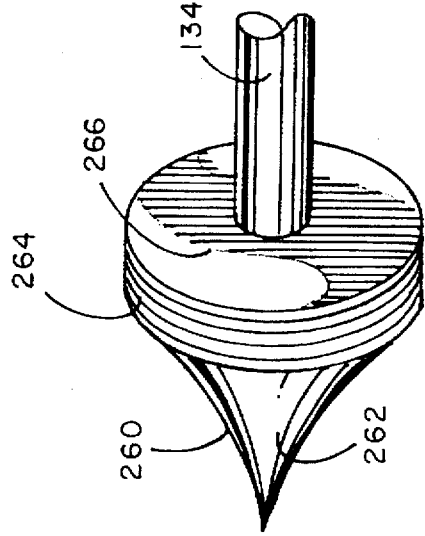
FIG. 21 is a side view of an alternative fifth puncturing headpiece of an obturator.
Figure 22:
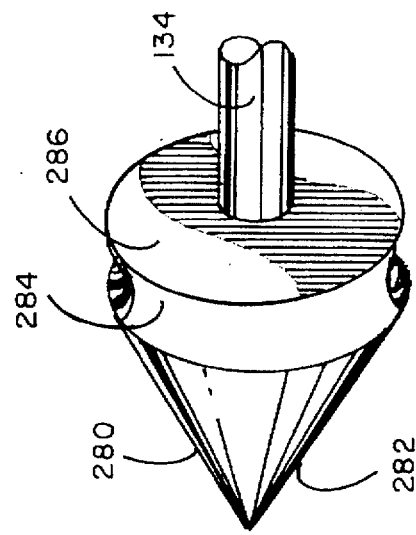
FIG. 22 is a side view of an alternative sixth puncturing headpiece of an obturator.

To demonstrate further the variety and degree of differences envisioned and intended when constructing a puncturing headpiece, the structural constructions exemplified by FIGS. 20–22 respectively are provided. As illustrated by FIG. 20, the puncturing headpiece 250 includes a buttressing region 254 as a part of the outer shell 252. The buttressing region 254 is a reinforced region for engaging and bending materials placed in contact with the outer shell when the puncturing headpiece is expanded. The puncturing headpiece 250 includes a base plate 256 and is integrated with the elongated shaft 134 (described previously herein).

In comparison, the puncturing headpiece 260 exemplified by FIG. 21 is a sharply tapered and contoured embodiment in which the outer shell 262 includes a spiral girth zone 264 suitable for deforming elastic materials. The base plate 266 conforms to and is integrated with the spiral zone 264.

Another alternative embodiment of the puncturing headpiece is illustrated by FIG. 22. In this embodiment, the puncturing headpiece 280 comprises an outer shell 282 and a concave-shaped or scalloped zone 284 which is joined to and integrated with the base plate 286. The concave-shaped configuration of the zone 284 is intended to aid the puncturing headpiece as it is expanded and contracted on-demand.

C. The Deformable Cuff

Figure 24:
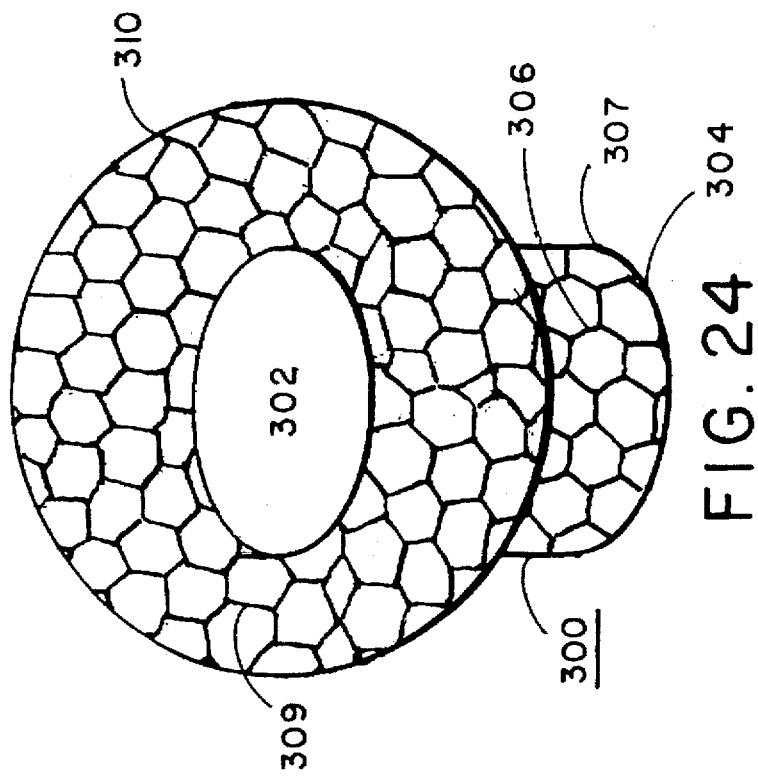
FIG. 24 is an overhead view of the preferred first deformable cuff of FIG. 23 after deformation.
Figure 23:
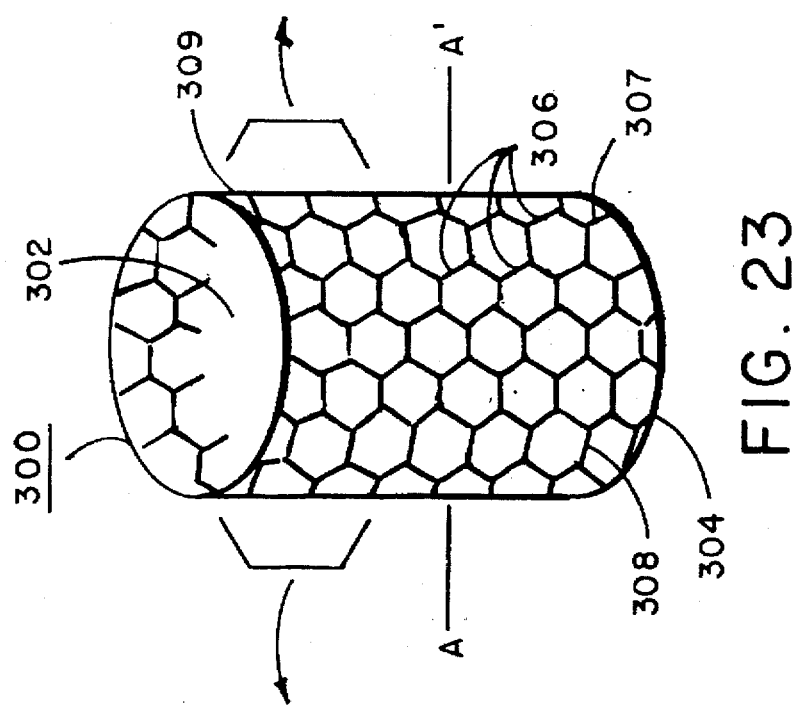
FIG. 23 is an overhead view of a preferred first deformable cuff in the original undeformed state.

A requisite component part of the catheter apparatus for creating a vascular bypass graft is the presence and use of a deformable cuff or flange, such as is illustrated by FIGS. 23 and 24 respectively. As illustrated and embodied therein, the deformable cuff 300 is a substantially cylindrical-shaped collar which is open at each of its ends 302, 304. The cuff 300 is hollow; is substantially round or oval (in cross-sectional view); and has determinable dimensions initially which can be deformed at will when sufficient force is applied to the sidewall 306. As an aide in controlling the intended deformation of the sidewall 306 on-demand via the intentional application of externally applied forces, it is most desirable that the material constituting the sidewall 306 of the cuff 300 be pre-stressed along the axis AA' as shown within FIG. 23; and that the material constituting the sidewall 306 be an open-weave pattern of resilient matter rather than take form as a solid mass of material. For this reason, the sidewall 306 illustrated within FIG. 23 appears as an open meshwork of wires 308 which are intertwined to form a substantially hexagonal pattern. This open meshwork of wires 308 provides the desired resiliency, flexibility, and deformation capability (particularly along the axis AA') such that the upper portion of the sidewall 306 can be deformed and flaired outwardly on-demand to yield the flaired-lip deformity 310 shown by FIG. 24.

It will be recognized and appreciated that the deform cuff shown by FIG. 24 is merely the result and consequence of exerting force along the uppermost portion 309 of the open meshwork of wires 308 above the axis AA' such that the upper sidewall 309 adjacent to the open end 302 has become expanded outwardly, flaired, and bent into a curved lip configuration in the deformed state. Note that the open meshwork of wires constituting the lower portion 307 of the sidewall 306 at the other open end 304 remains relatively stable and substantially unaltered in its original shape and state. The deformation has thus been controlled and the forces applied only to the upper portion from the AA' axis to cause the outwardly extending, flaired lip result. Moreover, the resulting flaired lip zone 310 retains structural strength and resiliency as an open meshwork of wires despite having been created by deformation. The ability of the cuff to be deformed in the manner illustrated by FIGS. 23 and 24 respectively is a requisite and necessary attribute and characteristic of each embodiment and construction for the deformable cuff.

The construction and design for the deformable cuff in the present invention is an example of the engineering principle that structural form follows intended function. As a requisite component part of the catheter apparatus and methodology for creating a vascular bypass in-vivo, the intended functions of the deformable cuff are twofold in nature: (1) the deformable cuff is intended to engage and become joined to a previously excised vascular segment which will serve as the bypass graft in-vivo; and (2) the deformable cuff is intended to be positioned within the internal lumen of an unobstructed major blood vessel (such as the aorta) and become deformed in-situ such that a portion of the cuff becomes positioned and secured to the internal lumen (the blood flow channel) of the unobstructed blood vessel permanently and in a fluid-tight manner. Thus, as illustrated by the embodiment of FIGS. 23 and 24, the uppermost region 309 of the cuff 300 is deformed on-demand into a flaired outwardly bent form which is intended to be secured within the lumen of the unobstructed artery or vein while the undisturbed sidewall portion 307 of the cuff is intended for engagement and juncture to the previously excised vascular segment which will serve as the bypass graft. However, because there is no specific pre-positioning or pre-alignment of cuff sections or portions as to ultimate or intended usage, it is immaterial and irrelevant structurally as to which end of the deformable cuff serves which intended function and purpose.

Several attributes and characteristics are commonly to be shared among all embodiments and constructions of the deformable cuff. These include the following:

(a) It is only required that the material constituting the cuff be deformable on-demand. For convenience and greater facility in achieving such deformity in the degree and at the time required, it is most desirable that the material forming the cuff be an open weave or meshwork rather than a solid mass which is considered to be more difficult to deform in a controlled manner. There is however no restriction or limitation at any time or under any intended use circumstances which necessitates an avoidance of a solid mass of material, either as a single sheet or as a laminated plank of material. Accordingly, the choice of whether to use an open meshwork or a solid mass of material is left solely to the discretion of the manufacturer and the surgeon.

(b) The deformable cuff need only be comprised of resilient, flexible, but deformable matter. A number of different compositions and formulations of material may be usefully employed when making a deformable cuff suitable for use with the present invention. Among the desirable materials are those listed within Table 2 below.

(c) After the deformable cuff has been manufactured using resilient materials, the completed cuff structure (prior to deformation) may be subsequently covered to advantage with one or more biocompatible coatings. These biocompatible coatings are intended to water-tighten the article and to facilitate the sewing of the excised vascular segment to the cuff as well as to reduce the interactions of the immune system with the vascular bypass graft after it has been secured to the blood vessels in their appropriate locations in-vivo. Such biocompatible coatings are conventionally known; will reduce the severity and duration of immune reactions which frequently disrupt or interfere with vascular bypass grafts; and are considered desirable in a majority of use instances in order to minimize the body reaction to vascular bypass surgery. A representative listing of biocompatible coatings deemed suitable for use with the deformable cuff is provided by Table 3 below.

TABLE 2

Deformable Materials

Metals and Alloys stainless steel;
nickel/titaniuim alloys;
aluminum/nickel alloys; and
graphite carbon and metallic blends of carbon

TABLE 2-continued

Deformable Materials

Synthetic Polymers polyamides such as nylon;
polyacrylates such as polyacrylic acid;
polycarbonates such as poly[2,2-bis(4-hydroxyphenyl)]propone; and
polysiloxones.

TABLE 3

Prosthetic Coatings

High temperature pyrongen-free carbon;
polytetrafluoroethylene (PTFE) and other polyhalogenated carbons;
Fibronection;
collagen;
hydroxyethyl methacrylates (HEMA); and
serum albumins.

(d) Although the embodiment of the cuff or collar prior to deformation exemplified by FIG. 23 appears as a geometrically regular and coherent structure, there is no requirement or demand that either the structure or configuration of any deformable cuff conform to these parameters. Accordingly, it will be recognized and understood that the deformable cuff structure need not be a completely encircling band or collar of deformable material. To the contrary, a U-shaped band or flange of material where the sidewall does not overlap or join and where a gapped distance separates the arms of the band or flange is both permitted and envisioned. Moreover, although the cylindrical-shaped format of the deformable cuff illustrated by FIG. 23 is highly desirable, there is no requirement that the diameter of the cuff prior to deformation be constant or consistent over the entire axial length of the cuff when manufactured. Thus, anisotropic cuff structures as well as isotropic constructions are intended and desirable. In this manner, the cuff in its initial state prior to deformation may have a variable internal diameter over the axial length of the article in which one open end may be either greater or lesser in size than the other open end; and there may be multiple increases and decreases in diameter size successively over the entire axial length of the cuff itself. All of these variations in construction and structure are within the scope of the present invention.

Figure 27:
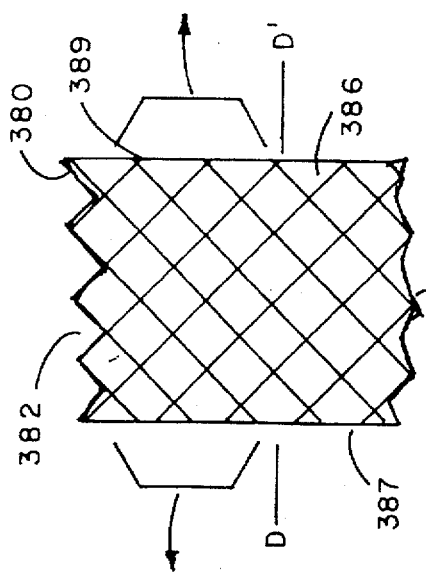
FIG. 27 is an overhead view of an alternative fourth deformable cuff in the original undeformed state.
Figure 26:
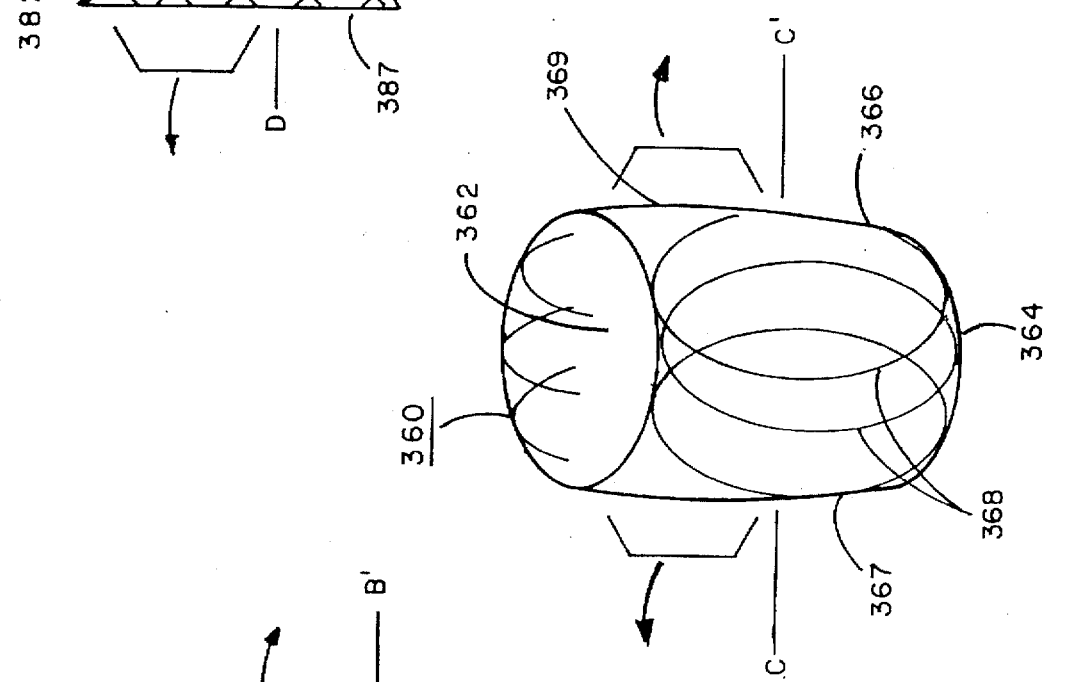
FIG. 26 is an overhead view of an alternative third deformable cuff in the original undeformed state.
Figure 25:
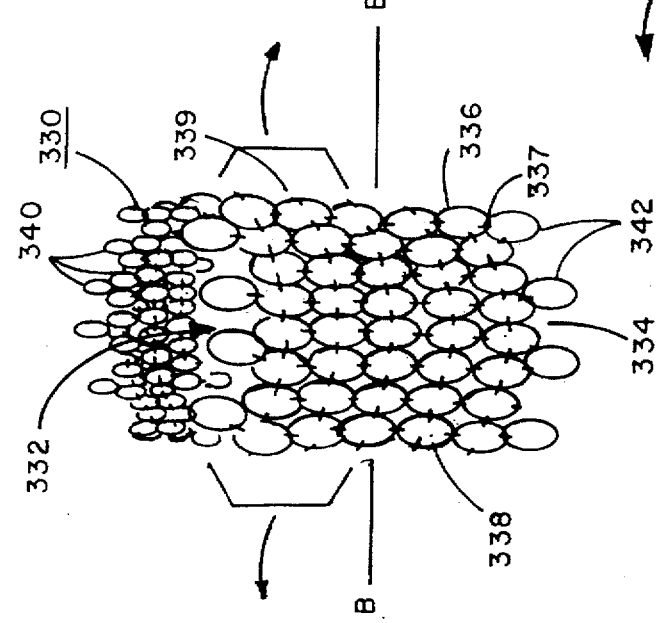
FIG. 25 is an overhead view of a preferred second deformable cuff in the original undeformed state.

To illustrate some of the modest variations and differences available and envisioned for a deformable cuff intended for use with the present invention, the alternative cuff embodiments illustrated by FIGS. 25, 26, and 27 are provided. As shown within FIG. 25, the deformable cuff or collar 330 appears as a cylindrical-shaped article having two open ends 332, 334 and a rounded sidewall 336. The body of the sidewall 336 is an open meshwork of closed loops 338, each closed loop being joined at multiple points along its perimeter to at least one other closed loop—thereby forming an open grid meshwork. A notable feature of the cuff construction within FIG. 25 are the outer edges of the open ends 332, 334. Each edge 340, 342 is formed by a closed loop which is far more easily bent and deformed than the closed-loop meshwork in the middle of the sidewall 336. In many instances, the availability of closed-loop edges 340, 342 provide an enormous benefit and advantage in deforming the cuff in-situ within the internal lumen of an unobstructed artery or vein. In addition, the deformable cuff 330 has been pre-stressed substantially at the midline along the axis BB' such that the upper most portion 339 of the cuff near the open end 332 and the edge 340 are more easily deformed and flaired outwardly as a consequence.

A third embodiment of a deformable cuff or flange is illustrated by FIG. 26. As shown therein, the deformable cuff 360 is formed primarily as a series of coiled wires whose overlapping and intersecting portions have been fused together to make a unitary article. The deformable cuff 360 thus has the two open ends 362, 364 and an open coiled sidewall 336 formed from the commonly fused coils of wire. The open lattice work of coiled wires 368 provides the flexible and resilient meshwork suitable for achieving the primary functions of the deformable cuff. Again, the sidewall 366 has been pre-stressed along the axis CC' such that the upper most portion 369 can be bent and deformed outwardly on demand using an expansion force.

Finally, a fourth alternative embodiment is provided by FIG. 27 in which the deformable cuff or band 380 is shown having two open ends 382 and 384. In this instance, however, the sidewall 386 is comprised of a solid sheet of material. Two features are included in this embodiment of the deformable cuff due to its construction using a solid sheet of resilient material as the sidewall 386 for the cuff. The sidewall 386 has been pre-scored to form cross-hatched squares over the axial length of the sidewall; and the pre-scored sidewall thus will deform far more easily and bend outwardly as shown when a expansion force is applied to the interior of the cuff. Similarly, the sidewall material has been pre-stressed along the axis DD' such that the upper most region 389 nearest the opening 382 will bend far more easily and in a controlled fashion when and as required by the user.

II. The Excised Vascular Segment To Be Used As A Bypass Graft

The preferred sources of blood vessels suitable for use as a vascular bypass graft are the saphenous veins. These veins constitute the superficial veins of the lower extremities and comprise both the greater (or long) saphenous and the lesser (or short) saphenous veins. Anatomically, the long saphenous vein begins on the medial side of the foot and ends in the fermoral vein below the inguinal ligaments; and the short saphenous vein begins behind the lateral malleous and runs up the back of the leg to end in the popliteal vein. However, if the saphenous veins of the particular patient are unsuitable or unavailable for any reason, either the cephalic or the basilic veins are very acceptable substitutes for use as a vascular bypass conduit. However, if these leg or arm veins are not available, synthetic or other biologic materials may also be used as substitutes.

The medical procedure to isolate and excise the saphenous vein of choice is conventionally known and considered a routine surgical technique. The saphenous vein is harvested under general anesthesia. An incision is first made in the medial malleolus, where the saphenous vein is often dilated. The saphenous vein is identified and then dissected with a single incision made along its course with scissors. Branches are doubly clamped with hemostatic clips and divided. The saphenous vein is then freed up and removed from the leg. The leg wound is closed with subcutaneous sutures and Steristrip adhesive over the incision. The vascular segment is prepared on a separate sterile table with adequate light and loupes, and branches are selectively ligated with 4-0 silk. An oval-tip needle on a syringe is inserted into the graft to gently dilate it by administering a balanced electrolyte solution (pH 7.4, chilled to 7 to 10 C) and 10,000 units/liter of heparin. A valvulotome is inserted into the vein graft segment and the valves clipped with a 3-mm right-angle stainless steel instrument with a highly polished ball tip on the right angle. The knife edge is protected and sharply splits the cusp, causing valvular incompetence. Measurements for the approximate lengths of the grafts may be made with umbilical tapes, and the appropriate lengths may be chosen before it is sewn to the cuff and coronary arteries.

III. The Introducer System

The introducer system comprises the catheter apparatus including the deformable cuff and a previously excised vascular segment in combination; and it is this introducer system which is utilized by the surgeon to perform the requisite acts and manipulations by which the excised vascular segment is delivered to and becomes secured within the lumen of the unobstructed major blood vessel (and subsequently anastomosed to the obstructed blood vessel at a site distal to the obstruction). For descriptive purposes and for increased clarity of comprehension, this description will intentionally limit itself to the use of the obturator illustrated by FIGS. 9 and 10 respectively, to the deformable cuff construction and structure illustrated previously by FIGS. 23 and 24 respectively, and to the use of a previously excised vascular segment taken from the long or short saphenous vein in the same patient. The introducer system represents and provides for the intentional placement and carriage of the excised vascular segment on the obturator, the engagement and juncture of the deformable cuff to one end of the excised vascular segment; and the proper orientation of the then engaged deformable cuff/excised vascular segment on the obturator with respect to its relationship to the puncturing headpiece.

The formation of the introducer system begins with the proper placement of the previously excised vascular segment (taken from the saphenous vein previously) upon the obturator. This manipulation is illustrated by FIG. 28 in which the excised vascular segment 400 is placed upon the elongated shaft 134 adjacent to but preferably not in direct contact with the base plate 126 of the puncturing headpiece 122. As shown therein, it is intended and preferred that the elongated shaft 134 will be inserted into the internal lumen 402 of the excised vascular segment 400 at the proximal end 138 held by the surgeon; and then the body of the vascular segment 400 is conveyed over the axial length of the elongated shaft 134 until a chosen position, typically 1–2 centimeters from the distal end adjacent to the puncturing headpiece 122 is reached. In this manner, the weight and body of the excised vascular segment 400 is carried on the elongated shaft 134; and it is desireable that the diameter of the elongated shaft 134 be only slightly smaller than the average diameter of the internal lumen 402 for the vascular segment 400. As a consequence, the excised vascular segment is adequately supported, carried, and transported by the elongated shaft during the entirety of the manipulations prior to entry into the body of the living patient as well as subsequent to the in-vivo perforation of the unobstructed major artery or vein. The manipulation illustrated by FIG. 28 is expected to be performed by the surgeon immediately after excising the vascular segment from the patient but prior to beginning the bypass graft surgery itself.

After the excised vascular segment 400 has been properly positioned on the elongated shaft 134 of the obturator 120, the deformable cuff (illustrated by FIG. 23 and described in detail previously herein) is desirably passed over the puncturing headpiece 122 and over the open end 404 to cover a small portion of the exterior surface over the excised vascular segment 400. It is desirable (but not absolutely necessary) that a gap distance (about 1–2 centimeters) separating the open end 404 from the puncturing headpiece 122 be maintained during the placement of the deformable cuff—as this will allow for easier positioning of the deformable cuff in a pre-chosen alignment and posture and a more controlled deformation on-demand. Once the deformable cuff 300 has been positioned over the vascular segment to the satisfaction of the surgeon, the lower region of the cuff covering the end exterior surface of the excised vascular segment 400 must be engaged and become joined to the vascular segment in a reliable and safe manner.

One preferred manner of engagement and juncture is for the surgeon to suture the open meshwork sidewall of the cuff directly to the vascular wall of the excised segment. This suturing is easily performed by the surgeon prior to beginning the grafting surgery and the sutures 420 will serve as the physical means for engaging and permanently joining a portion of the open meshwork of wires in the sidewall of the cuff to the excised vascular segment itself. The type of sutures 420, their placement, their number, and the linkage to the vascular wall of the excised segment are left to the personal discretion and choice of the surgeon.

Other means for engagement and juncture of the deformable cuff to the vascular wall of the excised segment also are commonly available. These include surgical staples; biocompatible adhesives; encircling ligatures; and a wide range of fasteners and closures. Any and all of these alternatives may be employed alone or in combination to achieve a reliable engagement and juncture.

After the deformable cuff has been engaged and joined to one end of the excised vascular segment then carried upon the elongated shaft of the obturator, the size of the puncturing headpiece 122 should be adjusted in shape and girth such that the diameter of the base plate 124 of the puncturing headpiece 122 preferably is equal to or slightly greater than the diameter of the open end 302 for the deformable cuff 300. This manipulation is also illustrated by FIG. 29 where the size of the base plate 126 is coextensive in diameter with the diameter of the open end 302 of the deformable cuff. In this preferred manner, the entirety of the puncturing headpiece 122 serves as a front section or first stage for the introducer system as a whole.

Figure 30:
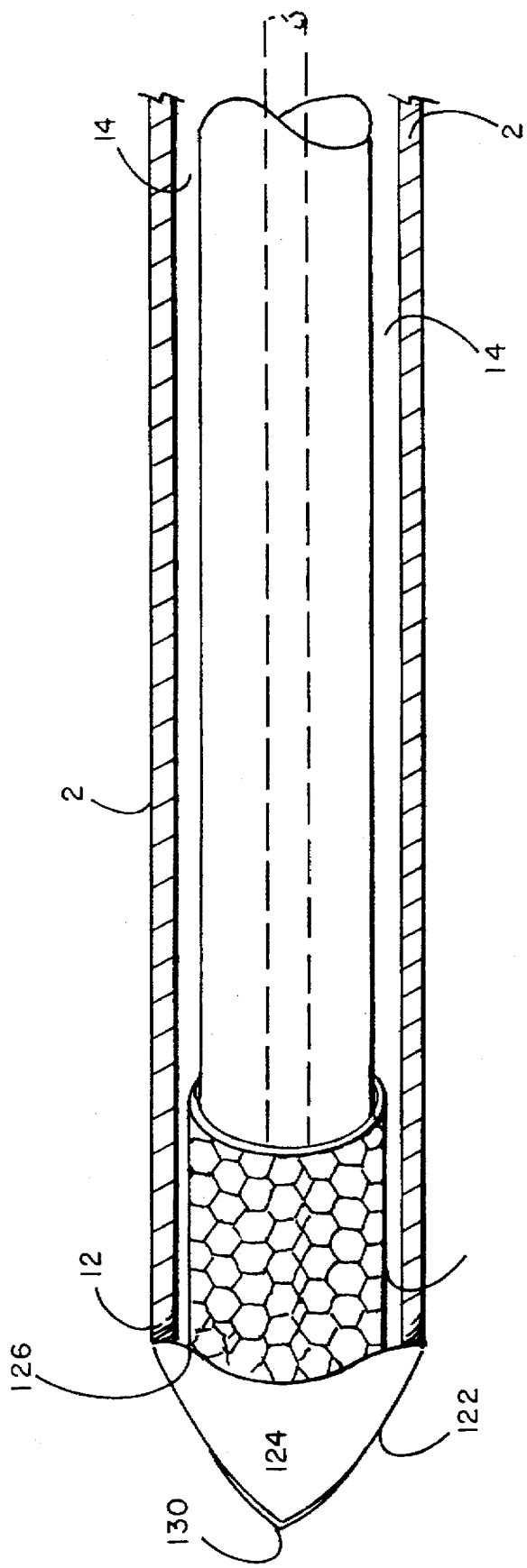
FIG. 30 is a partially exposed view of the introducer system as a whole.

The complete introducer system is illustrated by FIG. 30 in which the fully prepared obturator carrying the previously excised vascular segment to be used as a bypass graft and the deformable cuff have been positioned in advance; and the prepared obturator placed within the internal lumen of a catheter. As seen therein, the catheter is exposed in cross-sectional view and shows the hollow tube 2 of fixed axial length having a discrete proximal end (not shown), a discrete distal end 10 and an internal lumen 14 of pre-determined diameter sufficient to house the entirety of the prepared obturator (illustrated by FIG. 29). The distal end tip of the catheter is adapted for guidance of the catheter in-vivo to a chosen site where an unobstructed artery or vein is in anatomic proximity to an obstruction lying within another blood vessel; and the prepared obturator of FIG. 29 (including the previously excised blood vessel segment 400 and the deformable cuff 300) has been placed into the internal lumen of the catheter. The introducer system is now complete. As shown by FIG. 30, the surgeon may now begin the first steps for surgically delivering the introducer system into the thoracic cavity or other appropriate body region in order to create the vascular bypass graft.

IV. The Routing And Surgical Introduction Of The Controlling Catheter Into The Body Of The Living Human Catheterization involves a great deal of technical skill, some instrumentation and mature judgment in order to choose among the appropriate procedures and the various techniques which are now conventionally known and available for use. Clearly, because the present technique constitutes catheter intervention in critically ill patients, the physician or surgeon must be very familiar with the available anatomical alternatives in order to select the best routing for introducing the catheter, the best technique in order to access the thoracic cavity of the body where the obstructed artery and aorta exist, and to carefully select the timing and other operative conditions in order to achieve best results.

In general, catheterization can be performed using any duct, tube, channel, or passageway occurring naturally or surgically created for the specific purpose. Thus, among the naturally occurring passageways in the body are the anus; the alimentary canal; the mouth, ear, nose, or throat; a bronchus of the lung; the urethra; the vaginal canal and/or cervix; and any blood vessel of sufficient size of the central circulation in the body. Any of these routings are envisioned and expected to be used when and if appropriate. However, clearly a commonly used and the critical route of access is the introduction of catheters into the thoracic cavity and the arterial blood circulation adjacent to the heart.

For this reason, it is useful to briefly summarize the technique currently in use for introduction of catheters into the central blood circulation as an illustrative example of preferred catheterization techniques. There are two general methods currently in use. These are: (a) percutaneous introduction using needles and guidewires; and (b) direct introduction after surgical isolation of the blood vessel of choice. While either general method may be utilized at any site of the general circulation, practical and anatomical considerations including the site of the flawed therapeutic appliance will generally dictate which approach is most appropriate under the individual circumstances.

Figures 31A, 31B, 31C:
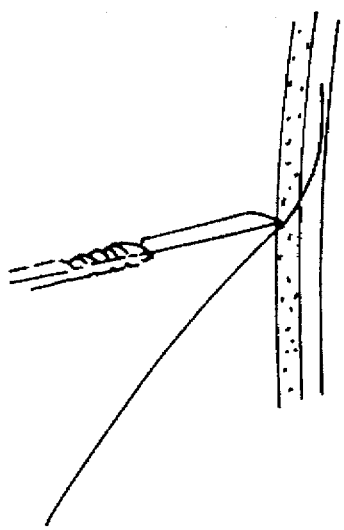
FIGS. 31A –31F are illustrations of the modified Seldinger technique conventionally used for percutaneous catherterization.
Figures 31D, 31E, 31F:
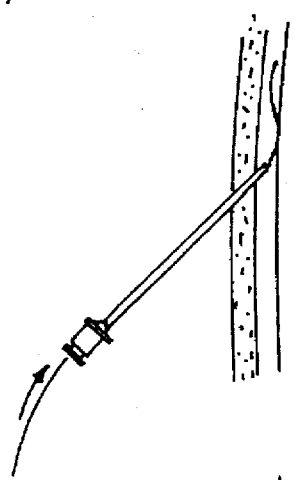

The modified Seldinger Technique:

The percutaneous introduction of a catheter is illustrated by the modified Seldinger technique which is shown by FIGS. 31A–31F respectively. FIG. 31A shows a blood vessel being punctured with a small gauge needle. Once vigorous blood return occurs, a flexible guidewire is placed into the blood vessel via the needle as shown by FIG. 31B. The needle is then removed from the blood vessel, the guidewire is left in place, and the hole in the skin around the guidewire is enlarged with a scalpel as shown by FIG. 31C. Subsequently, a sheath and a dilator is placed over the guidewire as shown by FIG. 31D. Thereafter, the sheath and dilator is advanced over the guidewire and directly into the blood vessel as shown by FIG. 31E. Finally, the dilator and guidewire is removed while the sheath remains in the blood vessel as illustrated by FIG. 31F. The catheter is then inserted through the sheath and fed through to reach the desired location.

The other general method for the introduction of catheters into the blood circulation is a direct surgical cutdown. The surgical cutdown approach is generally less favored and is typically used for the brachial or femoral approach. Cutdown procedure is often a complex surgery and is used only when no direct access is generally available. A far more complete and fully descriptive review of both these general catheterization techniques is provided by the texts of: *Diagnostic And Therapeutic Cardiac Catheterization*, second edition, 1994, Chapter eight, pages 90–110 and the references cited therein.

Accordingly, for purposes of practicing the present methodology, any and all conventionally known general catheterization procedures and techniques which are conventionally known and in accordance with good medical practice are explicitly intended to be utilized as necessary in their original format or in a modified form. All of these general catheterization routing and use techniques are thus envisioned and are deemed to be within the scope of the present invention.

General rules for choosing an appropriate site of body entry:

An axiomatic or general set of rules by which a surgeon or radiologist can chose a proper or appropriate site of entry for introducing the guiding catheter into the body of a patient for purposes of creating a vascular bypass in-vivo is as follows: (a) always pick the shortest and straightest pathway possible or available; (b) identify the chosen entry site on an existing and accessible unobstructed artery or vein, the larger the diameter of the unobstructed artery or vein the better; and (c) identify the location and orientation of the obstruction in the obstructed artery or vein and chose an entry site distal to the obstruction.

A favored approach to introducing the guiding catheter into the thoracic aorta:

Using the ascending aorta approach as a representative illustration and example:

(1) Under general anesthesia, the chest of the patient is prepared and draped in a sterile fashion.

(2) A three-inch incision is made to the left or right of the breast bone through which the surgeon operates.

(3) Three additional one-inch incisions then are made to insert a video camera, knife, surgical stapler, and other instruments.

(4) The ribs are separated, the thoracic cavity is entered, and the ascending thoracic aorta is exposed.

(5) The introducer system is then positioned at the chosen site on the ascending thoracic aorta.

V. The In-Vivo Placement Of The Vascular Bypass Graft Into The Lumen Of The Unobstructed Major Blood Vessel The method of the present invention utilizes the introducer system via the catheterization technique to create the vascular bypass graft between a major unobstructed blood vessel such as the aorta and an obstructed blood vessel in-vivo using a previously excised vascular segment as a conduit. This procedure is illustrated by FIGS. 32–41 collectively. It will be and appreciated, however, that while FIGS. 32–41 exemplify and illustrate the manipulations of the surgeon and the events in sequence leading to the creation of a vascular bypass, this description and the figures themselves present a greatly simplified presentation and explanation of the medical procedure, the technical skills required, and the safety measures taken for the patient's benefit medically.

Figure 32:
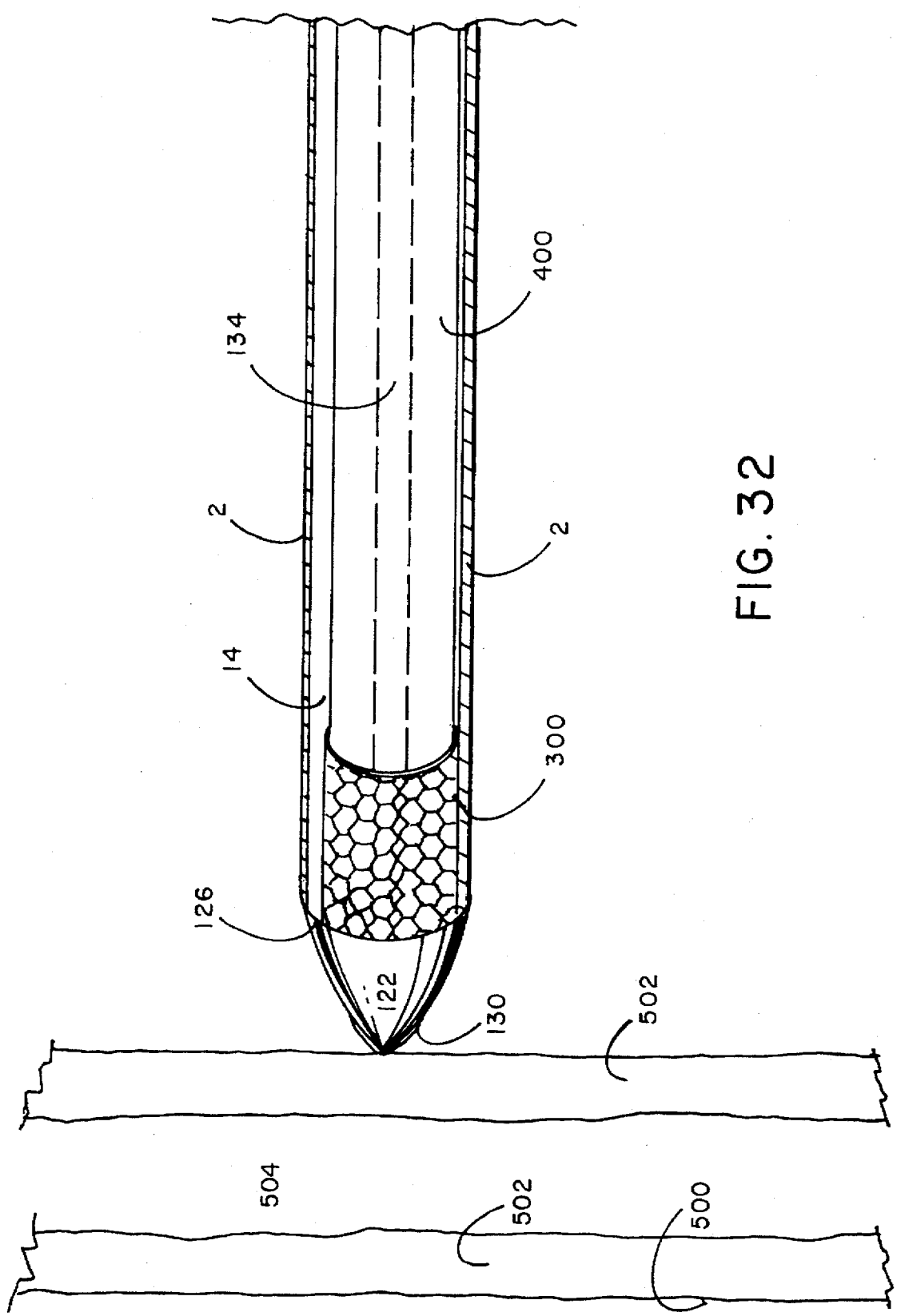
FIG. 32 is a partially exposed view of the introducer system in the correct position at the exterior wall of an unobstructed blood vessel in-vivo.

After the controlling catheter has been routed and surgically introduced into the body of the living human in the manner described previously herein, the first critical stage for the process is reached as shown by FIG. 32. The illustration of FIG. 32 (as well as FIGS. 33–41 respectively) are shown as partially exposed views in order to show more easily the detailed placement and orientation of the prepared obturator carrying the deformable cuff and previously excised vascular segment in combination.

As seen within FIG. 32, the major artery such as the aorta 500 is shown in partial cross-sectional exposed view to reveal the thickness of the arterial wall 502 and the internal lumen 504.

The catheter and the prepared obturator are as described in detail previously herein and illustrated by FIG. 30. It will be noted that the puncturing headpiece 122 of the obturator 120 is positioned within the lumen of the catheter 2 such that the perforating end tip 130 is in direct contact with the arterial wall 502 at the chosen vascular site. The puncturing headpiece 122 is of sufficient size such that the entirety of the deformable cuff 300 and the joined vascular segment 400 lie directly behind and are in axial alignment with the puncturing headpiece 122 and the elongated shaft 134. When positioned as shown by FIG. 32, the prepared obturator is properly placed for piercing and penetrating the arterial wall on-demand.

Figure 33:
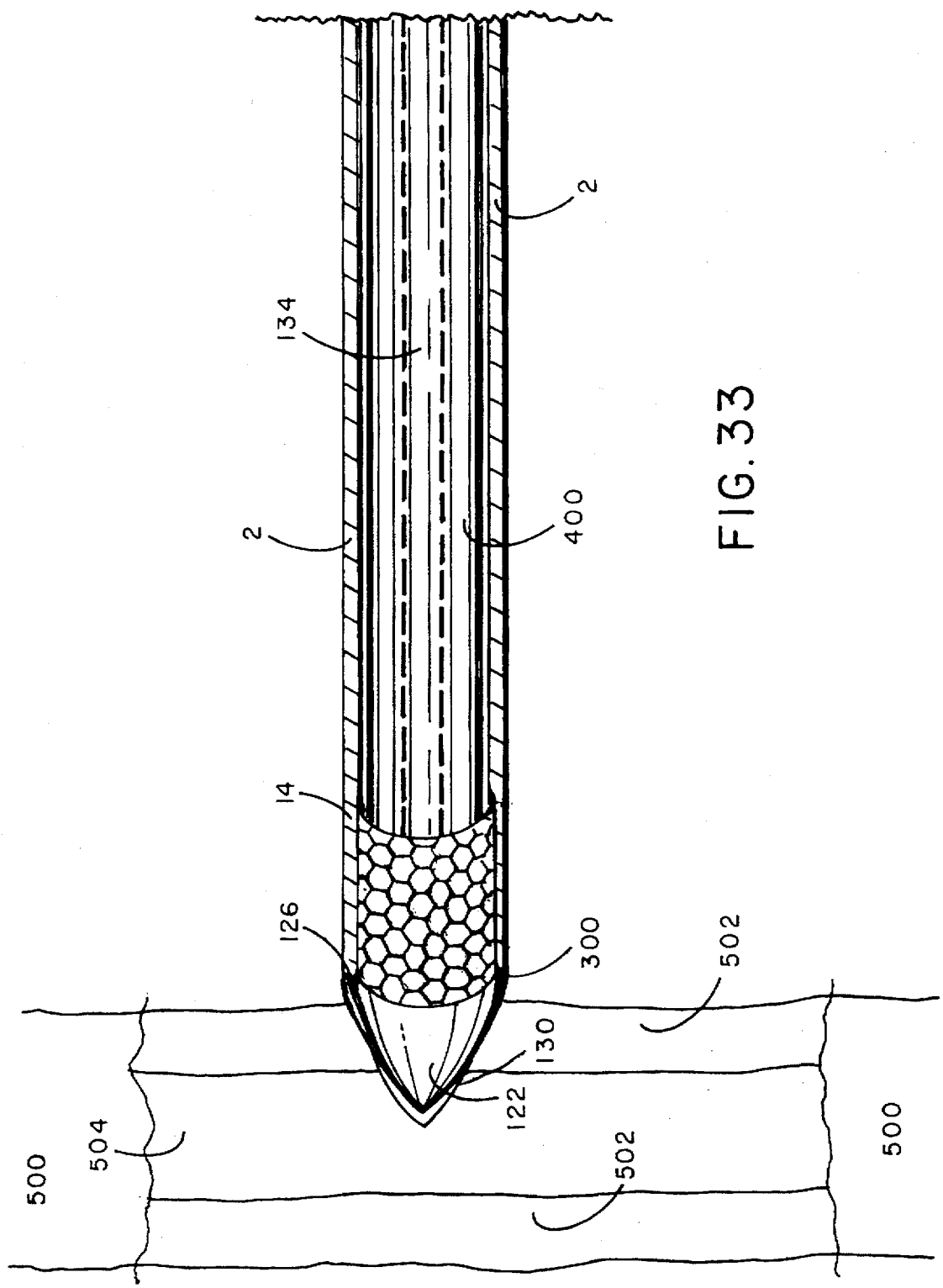
FIG. 33 is a partially exposed view of the prepared obturator penetrating the vascular wall of the unobstructed blood vessel in-vivo.

When the surgeon extends the prepared obturator within the internal lumen of the catheter 2, the result is illustrated by FIG. 33. As seen therein, the perforating end tip 130 has pierced and punctured the arterial wall 502 and been advanced into the arterial lumen 504. The initial hole in the arterial wall 502 made by the perforating end tip 130 is widened into a passageway as a consequence of the puncturing headpiece 122 following the entry path created by the perforating end tip. As the puncturing headpiece 122 penetrates the arterial wall 502, the size of the puncture in the arterial wall becomes widened and enlarged to conform to and accommodate the configuration and the girth of the puncturing headpiece in its entirety. The configuration and overall size of the puncturing headpiece 122 thus serves as the means for widening the initial puncture made by the perforating end tip 130 such that the entire girth and overall diameter of the obturator (complete with the deformable cuff and excised blood vessel segment in combination) can subsequently pass through the enlarged hole in the arterial wall.

As the prepared obturator is extended further across the thickness of the arterial wall 502 through the enlarged passage, the penetrating headpiece 122 is extended farther into the arterial lumen 504 until at least the upper portion of the deformable cuff 300 has advanced far enough such that the cuff 300 has itself entered the internal lumen of the blood vessel. This sequence of events and result is illustrated by FIG. 34.

Subsequently, after the upper portion of the deformable cuff 300 has advanced into the arterial lumen 504, the surgeon holding and controlling the proximal end of the catheter (not shown) activates the means for contracting the girth of the puncturing headpiece 122 while the headpiece lies extended in the arterial lumen 504. This manipulation and result is illustrated by FIG. 35. As seen therein, the puncturing headpiece 122 has been reduced in overall size and shows a diminished diameter or girth in comparison to its initial size as shown previously via FIGS. 31–34 respectively. The reduced overall size and altered configuration of the puncturing headpiece 122 lying disposed within the arterial lumen in-vivo is a critical manipulation and step of the methodology.

After the puncturing headpiece has been reduced in overall size and has a diminished girth, the overall diameter of the contracted puncturing headpiece 122 is smaller in overall diameter and size than the diameter of the deformable cuff disposed directly behind the headpiece. Due to the reduced size of the puncturing headpiece 122, the deformable cuff and engaged vascular segment carried upon the elongated shaft 134 of the obturator may then be advanced farther through the puncture in the arterial wall 502 and be further advanced over the puncturing headpiece 122 into the arterial lumen 504. This manipulation and result is illustrated by FIG. 36.

It is important to recognize and note that a substantial portion of the deformable cuff 300 has been extended over the outer shell 124 of the puncturing headpiece 122 in the manner illustrated by FIG. 36. Moreover, concomitant with the extension of the deformable cuff 300 into the arterial lumen 504, the engaged and joined vascular segment 400 is concurrently advanced and extended through the enlarged puncture or hole in the arterial wall 502 at the chosen site. The degree to which the end of the engaged vascular segment 400 is advanced lies at the discretion of the surgeon performing this methodology. If the surgeon so chooses, the end of the excised vascular segment joined to the deformable cuff 300 may be extended only through the arterial wall 502 but not markedly into the arterial lumen 504 itself. In the alternative, the surgeon may choose to advance the end of the engaged vascular segment 400 further and thus position the open end of the vascular segment 400 well within the internal lumen of the artery itself. The degree of entry and advancement for the deformable cuff and the engaged vascular segment thus is the choice and at the discretion of the surgeon at all times.

After the deformable cuff 300 and the engaged vascular segment 400 have been advanced such that each has penetrated the arterial wall 502 and a portion of the deformable cuff 300 has been extended to cover in part the contracted puncturing headpiece 122 to the surgeon's personal discretion and accommodation, the surgeon will then activate the means for expanding the puncturing headpiece 122. At the time of activating the expansion means for the puncturing headpiece 122, it is critical to recognize and appreciate that the uppermost region of the deformable cuff 300 encompasses and overlies the outer shell 124 and base plate 126 of the headpiece 122—as shown by FIG. 36. It is not necessary that the deformable cuff actually cover and envelope the perforating end tip 130, although if the surgeon chooses to extend the deformable cuff so far into the internal lumen of the artery, the surgeon may do so at his discretion. In each instance, however, when the means for expanding the puncturing headpiece 122 are inactivated, the overall size and girth of the puncturing headpiece will markedly increase. In the course of expanding in overall size and dimensions, the puncturing headpiece will then make contact with the upper position of the deformable cuff 300 which has been prepositioned to envelope and encompass the headpiece. Thus, as the overall size and girth of the puncturing headpiece 122 increases with time, the outer shell 124 of the headpiece will engage the upper portion of the overlying deformable cuff 300; and consequently apply expansion force to the sides of the deformable cuff in-situ.

As the controlled expansion force applied by the increasing girth of the puncturing headpiece 122 increases, the sidewall 306 of the cuff will deform, be bent outwardly, and become flaired and flattened out within the internal lumen 504 of the artery 500. Then, as the puncturing headpiece 122 expands in overall size and girth in ever greater degree, the deformed sidewall of the cuff 300 will become more flattened; and will come to lie against the interior surface of the arterial wall 502; and thereby become secured to the arterial wall in a permanent manner. This manipulation and result is illustrated by FIG. 37.

As shown within FIG. 37, the puncturing headpiece 122 has been greatly enlarged and expanded as the headpiece lies within the arterial lumen 504. The controlled expansion of the puncturing headpiece with the concomitant deformation and flairing of the uppermost portion of the cuff 300 occurs within the blood flow channel of the artery and is intended to be performed without substantially diminishing the rate of blood through the lumen of the artery or causing the heart of the patient to stop at any time. The intentional and controlled deformation of the cuff 300 along its upper region as it lies disposed within the arterial lumen 504 causes a permanent flairing of the open meshwork of wires 308 forming the sidewall 306. The deformed sidewall is bent, maneuvered, and flaired solely by the expansion force of the puncturing headpiece. No other tool, article, or device is needed or utilized in order to cause a controlled expansion force and to create the deformation of the cuff while disposed within the central blood channel of the artery in-vivo.

After the cuff has been controlably deformed within the arterial lumen 504 and become secured to the interior surface of the arterial wall 502 to the personal satisfaction of the surgeon, the means for contracting the puncturing headpiece 122 are then once again activated. This contraction of the puncturing headpiece 122 serves to diminish the overall size and configuration of the headpiece and markedly reduces the girth of the outer shell 124 such that the overall diameter or girth of the puncturing headpiece becomes approximately equal to or less than the diameter of the elongated shaft 134. The degree of contraction for the puncturing headpiece 122 is desirably chosen and correlated to the diameter of the engaged vascular segment 400 then carried on the elongated shaft 134. By conforming the overall size and girth of the puncturing headpiece to a size approximately equal to the diameter of the elongated shaft 134, the surgeon is confident that the overall diameter of the properly contracted puncturing headpiece is now smaller than the internal lumen of the engaged vascular segment; and therefore, the contracted puncturing headpiece will then be able to enter and pass completely through the internal lumen of the engaged vascular segment without meaningfully injuring or altering the internal surface of the blood flow channel itself. The act of reducing the overall size and girth of the puncturing headpiece with the resulting consequence that it may pass through and exit the artery 500 is illustrated by FIG. 38.

After the puncturing headpiece has been contracted to a minimal overall size and girth, the entirety of the obturator 120 is withdrawn by the surgeon holding the proximal end of the obturator. The reduced size of the puncturing headpiece 122 shown previously by FIG. 38 will pass through the interior of the deformed cuff 300 which is now secured in part within the internal lumen of the artery; and also pass through the internal lumen of the engaged vascular segment 400 which has been previously joined to the cuff in permanent fashion. The act of removing the obturator is quickly accomplished by the skilled surgeon; and the act of removal serves to isolate the now deformed sidewall 306 of the cuff 300 secured to the interior surface of the arterial wall 502. The deformed cuff 300 and the engaged vascular segment 400 and remain permanently secured and attached to the blood flow channel of the major artery in a manner which permits arterial blood to enter through the deformed cuff into the internal lumen of the vascular segment without meaningful major alteration of the primary artery and without major destruction of vascular tissues at the site of graft bypass juncture. To ensure that the placement of the deformed cuff and engaged vascular segment is fluid-tight, the surgeon then preferably applies a biocompatible adhesive 530 to the exterior surface of the arterial wall 502 at the puncture site. The biocompatible adhesive 530 is desirably spread over the sidewall 306 of the cuff 300 at the exterior surface of the puncture site as is shown by FIG. 39. The biocompatible adhesive dries quickly; forms a permanent and fluid-tight seal; and will not degrade or cause irritation to either the artery or the grafted vascular segment now to be used as a shunt. Note also that the catheter tube has desirably also been removed prior to the placement of the biocompatible adhesive at the juncture site on the arterial wall. This catheter removal step is preferred in order to have better access to the deformed cuff at the vascular site and the point of juncture.

A number of different biocompatible adhesives may be employed to seal permanently the puncture site in the manner shown by FIG. 39. A representative but nonexhaustive listing of such biocompatible adhesives is provided by Table 4 below.

TABLE 4

Biocompatible Adhesives

Adhesives fibrin glue;
histacryl (butyl-2-cyanoacrylate) tissue adhesive;
cyanoacrylates;
liquid silicones;
epoxy resins; and
polyurethane adhesives.

The overall result of this procedure is illustrated by FIG. 40 in which the uppermost region of the cuff sidewall 306 has been deformed and flaired outwardly into the internal lumen 504 of the artery 500. The open meshwork of wires 308 has aided and assisted the ease and speed by which the deformed sidewall has been bent and extended into the internal arterial lumen and become secured to the interior surface of the arterial wall 502. Also, the placement of the biocompatible adhesive 503 at the puncture site and graft juncture places the bypass conduit in a fluid-tight setting permanently such that the engaged vascular segment 400 has become attached to and is in blood flow communication with the arterial blood in an unobstructed manner. The placement and securing of the vascular graft to the major unobstructed artery is thus complete in all respects.

The other end of the excised vascular segment 400 is then conventionally attached to the obstructed blood vessel at a site distal to the obstruction itself. The manner of joining the other open end of the grafted vascular segment to the obstructed artery or vein may be achieved conventionally by anastomosis, with or without sutures and with or without use of tissue adhesives by the surgeon. It will be noted and appreciated also, that the surgeon may in fact intentionally create an aperture in the wall of the grafted vascular segment 400, introduce the obturator 120 into the internal lumen of the vascular segment; place a second deformable cuff 300 in proper position; and then engage the cuff to the second open end of the vascular segment in the manner described previously. If the surgeon so chooses, therefore, the entirety of the introducer system and the catertization methodology may be repeated at the chosen site on the obstructed blood vessel. Nevertheless, it is generally expected that in most instances, the surgeon will prefer to perform conventional anastomosis as the means for joining the other open end of the blood vessel segment to the obstructed artery or vein. This is illustrated by FIG. 41.

The entire catheterization methodology for creating a vascular bypass graft or shunt has been shown and described in detail via FIGS. 33–41 inclusive. Each essential manipulation or required act has been illustrated in detail and described in depth. Nevertheless, to assure a complete and comprehensive presentation of the methodology as a whole, a summary recitation of the preferred surgical procedures using the catheter apparatus, the introducer system, and the methodology is provided hereinafter.

VI. Summary of the Preferred Surgical Procedures Using the Catheter Apparatus and Method The catheter apparatus and methodology comprising the present invention provides an approach designed to allow surgeons do multiple bypass using vein bypass grafts in a minimally invasive way. This procedure allows a simpler way to place the vein grafts proximally to the aorta and distally to the coronary artery without using a heart-lung machine and without need for stopping the heart. Small incisions are first made between the ribs; a video camera and instruments with long handles are inserted; and, under the direct visualization, the aorta is punctured to create a proximal graft to anastomosis (aortotomy) using a specially prepared catheter introducer system which internally carries a deformable cuff and a previously excised vascular segment.

The deformable cuff is made of nitinol wire mesh (or other metals such as stainless steel or polymers); and is preferably coated with prosthetic material such as PTFE. The cuff will become anchored by deformation inside the aortic wall and be secured and blood-leak-proven outside the aortic wall by subsequently applying a tissue adhesive. This deformed cuff will provide a secure sutureless aortic anastomosis for the bypass vein graft. The proximal part of the vein graft is preferably sewn to the cuff. The bypass graft is then distally anastomosed to the coronary artery, which can be done either by the conventional way with sutures or by applying tissue adhesive between the adjacent outer walls of the bypassable coronary artery and the bypass vein graft without sutures.

This unique procedure simplifies the complexity of the conventional coronary artery bypass surgery and makes the surgery less invasive. Moreover, this technique provides a critical advantage over the conventional bypass surgery (using excised vein grafts), or the thoracoscopic minimally invasive surgery (using an internal mammary vein graft). Also, it will shorten the operation time and make the coronary bypass surgery safer and more cost-effective.

Thoracotomy and Aorotocoronary Bypass:

After cutting through the muscle and other tissue of the anterior chest, the surgeon separates a rib from the breast bone and cuts a piece of the cartilage at the detached end to provide working space for the aortotomy and placement of the proximal graft anastomosis.

The bypassing of the vascular blockage increases blood flow to the heart. The optimal environment for the vascular anastomosis is a motionless, dry field. In conventional coronary bypass surgery, this environment can be obtained by total cardiopulmonary bypass and cardioplegia techniques to arrest the heart. However, in minimally invasive coronary bypass surgery, it is performed without cardiopulmonary bypass and without stopping the heart. Instead, the heart beat is slowed down with cardiac medications such as calcium channel blockers, beta-blockers and hypothermia.

Creation of the proximal anastomosis

The ascending aorta is first palpated before creation of the aortotomy to determine the proper location of the aorta for aortotomy and delivery of the introducer system. The ascending aorta is preoperatively evaluated by means of CT scan or MRI to exclude the patient with severe atherosclerosis of the aorta, which may interfere with creation of the aorotomy and increase possible associated complications such as dissection and embolization of the plaques. When the ascending aorta is shown to be moderately thick by CT or MRI, the deformable cuff is larger (7 to 8 mm outer diameter) than usual (5 to 6 mm outer diameter) and may be placed in the aorta to prevent narrowing at the proximal anastomosis.

This technique involves safe and simple placement of the proximal anastomosis of the vein graft without clamping of the aorta and without using heart-lung machine. The proximal part of the ascending thoracic aorta is first exposed and punctured with an obturator that carries a cuff and a previously excised blood vessel segment within it (FIGS. 32–34). The cuff is made of a nitinol wire mesh (or other metals such as stainless steel or polymers) and has a flared end, which will firmly anchor its deformed and flared proximal end against the inner wall of the thoracic aorta. The cuff is desirably covered with a prosthetic material (such as Dacron and PTFE, etc.) to prevent any leaking of blood through the mesh cuff. Continuous 5-0 Prolene is used for the anastomosis between the cuff and the grafts when the saphenous vein is the usual size (5 to 6 mm).

After the aortic puncture, the proximal end of the cuff vein graft is deformed and released into the arterial lumen as the obturator is being retracted (FIGS. 35–39). The vein graft is slowly pulled back until the cuff is anchored against the internal wall of the aorta via its deformed flared end. Once the cuff and the proximal end of the vein graft is internally anchored, then tissue adhesive (glue) is applied around the exit site of the graft (between the graft and the adjacent outer wall of the aorta) so that any possibility of leakage of blood will be minimized and also to secure further the proximal anastomosis. The upper end of the vein graft is clamped to stop blood flow; and drugs are injected into the lower end to prevent it from going into spasm while the surgeon works on the coronary anastomosis.

Exposure of the coronary arteries and creation of the distal anastomosis

The sac covering the heart is cut, the thin coronary artery is under direct view. The patient is given calcium channel blockers and a beta blocker intravenously to slow the heart, which facilitate that the surgeons thread the stitches through the artery. The coronary artery vessels to be bypassed is identified and exposed after opening either hemithorax.

With a sharp knife, the surgeons cut into the coronary artery (arteriotomy). The arteriotomy is then increased to 8 to 12 mm with Pott's or reversed acute angle scissors. The internal diameter of the coronary artery is calibrated and the size recorded. The distal part of the graft that has been set aside is sewn to the coronary artery with the same fine sutures that are used in standard bypass operations (FIG. 41). A continuous suture of 6-0 or 7-0 Prolene is begun in the heel of the vein graft with a narrow mattress stitch and continued to the proximal portion of the coronary artery. Approximately 1-mm bites are taken as the suture line is continued around one side to the distal end. At that point the suture line may be interrupted with one or more sutures. With smaller vessels interrupted sutures are easy to insert and less likely to constrict the anastomosis. With larger vessels (2.5 mm or greater) the suture line may be continued without interruption around the distal end. The other end of the original stitch is continued on the contralateral side, and the anastomosis is terminated at the midpoint of the arteriotomy. Anastomotic patency is checked in both directions. A flush of clear solution through the needle may be of aid during the performance of the distal anastomosis to keep the anastomotic area free of blood. Alternatively, the coronary artery and bypass vein grafts can be anastomosed by applying tissue adhesive (glue) between their adjacent outer walls, without using sutures, which facilitates and expedites the coronary anastomosis when application of tissue adhesive make two structures bonded in a side-to-side fashion, a fenestration in a proper length is made between them by putting an incision extending from the lumen of vein graft to the lumen of the coronary artery with a knife inserted via the distal open end of the graft. After this, the open distal end of the vein graft is sewn as a blind end.

This procedure is repeated until all the blocked vessels to be revascularized are bypassed. After checking for bleeding, the surgeon closes the chest.

The present invention is not to be limited in scope nor restricted in form except by the claims appended hereto.

What I claim is:

1. A catheter apparatus for creating a vascular bypass on-demand between an unobstructed blood vessel and an obstructed blood vessel in-vivo using a previously excised vascular segment as a conduit, said vascular bypass catheter apparatus comprising:
    a catheter suitable for introduction into and extension through the body in-vivo, said catheter being comprised of
        (a) a hollow tube of fixed axial length having a proximal end, a distal end, and at least one internal lumen of predetermined diameter, and
        (b) a distal end tip adapted for guidance of said catheter in-vivo to a chose site wherein an unobstructed blood vessel is in anatomic proximity to an obstruction lying within another blood vessel;
    an obturator for on-demand introduction and passage through said catheter to a chosen site on the unobstructed blood vessel in-vivo, said obturator comprising
        (1) an expandable and contractible puncturing headpiece for puncture of and entry into the lumen of an unobstructed blood vessel, said puncturing headpiece being expandable on-demand to a size greater than the diameter of said internal lumen of said catheter and being contractible on-demand to a size less than the diameter of said internal lumen of said catheter,
        (2) a perforating end tip on said puncturing headpiece to facilitate the perforation of a blood vessel wall at the chosen vascular site in-vivo
        (3) an elongated shaft of fixed axial length integrated with said puncturing headpiece, said elongated shaft being configured for the carrying and transport of the previously excised vascular segment with said internal lumen of said catheter to the chosen site on the unobstructed blood vessel in-vivo,
        (4) means for expanding and contracting said puncturing headpiece of said obturator on-demand; and
    a deformable cuff for positioning over said elongated shaft adjacent to said puncturing headpiece of said obturator together with a previously excised vascular segment
        (i) wherein, prior to the perforation of the unobstructed blood vessel in-vivo by said puncturing headpiece of said obturator, at least a portion of said deformable cuff has been engaged and joined to one end of the excised vascular segment then carried by said elongated shaft of said obturator,
        (ii) and wherein, after the perforation of the unobstructed blood vessel in-vivo by said puncturing headpiece of said obturator, at least part of said engaged cuff is extended into the lumen of the unobstructed blood vessel, is partially deformed in-situ by an expansion of said puncturing headpiece of said obturator, and said engaged cuff becomes attached via said partial deformation to the interior of the unobstructed blood vessel,
        (iii) and whereby said cuff engaged one end of the previously excised vascular segment become secured to and placed in blood flow communication with the unobstructed blood vessel and serves as vascular conduit means for bypassing an obstruction and restoring blood flow from the unobstructed blood vessel to the obstructed blood vessel.

2. The catheter apparatus as recited in claim 1 wherein said deformable cuff is comprised of metal.

3. The catheter apparatus as recited in claim 1 wherein said deformable cuff is comprised of a polymeric material.

4. The catheter apparatus as recited in claim 1 wherein said deformable cuff is overlaid with prosthetic matter.

5. The catheter apparatus as recited in claim 1 wherein said deformable cuff comprises an open meshwork.

6. The catheter apparatus as recited in claim 1 wherein said deformable cuff comprises a solid mass of material.

7. The catheter apparatus as recited in claim 1 wherein said means for expanding and contracting said puncturing headpiece further comprises a mechanical assembly.

8. The catheter apparatus as recited in claim 1 wherein said means for expanding and contracting said puncturing headpiece further comprises a hydraulic assembly.

9. A catheterization method for creating a vascular bypass on-demand between an unobstructed blood vessel and an obstructed blood vessel in-vivo using a previously excised vascular segment as a conduit, said vascular bypass catheterization method comprising the steps of:
    providing a catheter suitable for introduction into and extension through the body in-vivo, said catheter being comprised of
        (a) a hollow tube of fixed axial length having a proximal end, a distal end, and at least one internal lumen of predetermined diameter, and
        (b) a distal end tip adapted for guidance of said catheter in-vivo to a chosen site wherein an unobstructed blood vessel is in anatomic proximity to an obstruction lying within another blood vessel;
    providing an obturator for on-demand introduction and passage through said catheter to a chosen unobstructed blood vessel in-vivo, said obturator comprising
        (1) an expandable and contractible puncturing headpiece for puncture of and entry into the lumen of an unobstructed blood vessel, said puncturing headpiece being expandable on-demand to a size greater than the diameter of said internal lumen of said catheter and also being contractible on-demand to a size less than the diameter of said internal lumen of said catheter,
        (2) a perforating end tip of said puncturing headpiece to facilitate the perforation of a blood vessel wall at the chosen site in-vivo
        (3) an elongated shaft of fixed axial length integrated with said puncturing headpiece, said elongated shaft being configured for the carrying and transport of a previously excised vascular segment with said internal lumen of said catheter to the chosen vascular site on the unobstructed blood vessel,
        (4) means for expanding and contracting said puncturing headpiece of said obturator on-demand;
    placing a previously excised vascular segment on the elongated shaft adjacent to said puncturing headpiece of said obturator;
    positioning a deformable cuff over said elongated shaft and one end of the previously excised vascular segment lying adjacent to said puncturing headpiece of said obturator such that at least a portion of said deformable cuff engages and is joined to the end of the excised vascular segment;

perforating the unobstructed blood vessel at the chosen site in-vivo using said puncturing headpiece of said obturator;

extending at least part of said engaged cuff into the lumen of the unobstructed blood vessel;

partially deforming said extended cuff in-situ by an expansion of said puncturing headpiece of said obturator
  (i) whereby said engaged cuff becomes attached via said partial deformation to the interior of the unobstructed blood vessel,
  (ii) and whereby said cuff engaged one end of the previously excised vascular segment become secured to and placed in blood flow communication with the unobstructed blood vessel; and joining the other end of the secured vascular segment to the obstructed blood vessel at a chosen site distal to the obstruction, said joined segment serving as vascular conduit for means for bypassing the obstruction and restoring blood flow from the unobstructed blood vessel to the obstructed blood vessel.

10. The catheterization method as recited in claim 9 wherein the vascular bypass is created between an unobstructed artery and an obstructed artery.

11. The catheterization method as recited in claim 9 wherein the vascular bypass is created between an unobstructed vein and an obstructed vein.

12. The catheterization method as recited in claim 9 wherein said vascular bypass is created between an artery and a vein.

* * * * *